(12) United States Patent
Cao et al.

(10) Patent No.: US 9,913,828 B2
(45) Date of Patent: *Mar. 13, 2018

(54) BENZOTHIAZOLONE COMPOUND

(71) Applicant: Novartis AG, Basel (CH)

(72) Inventors: Jun Cao, Changshu (CN); Bernhard Erb, Gipf-Oberfrick (CH); Robin Alec Fairhurst, Riehen (CH); Arnaud Grandeury, Helfrantzkirch (FR); Shinji Hatakeyama, Basel (CH); Magdalena Koziczak-Holbro, Basel (CH); Xinzhong Lai, Changshu (CN); Philipp Lustenberger, Allschwil (CH); Bernd Ulrich Riebesehl, Loerrach (DE); Nicola Tufilli, Moehlin (CH); Thomas Ullrich, Bottmingen (CH); Xiang Wu, Changshu (CN); Jianguang Zhou, Suzhou (CN)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,579

(22) Filed: Jun. 10, 2016

(65) Prior Publication Data

US 2016/0279107 A1 Sep. 29, 2016

Related U.S. Application Data

(60) Continuation of application No. 14/817,175, filed on Aug. 3, 2015, now abandoned, which is a continuation of application No. 14/566,021, filed on Dec. 10, 2014, now abandoned, which is a division of application No. 13/603,990, filed on Sep. 5, 2012, now Pat. No. 8,933,108.

(30) Foreign Application Priority Data

Sep. 6, 2011 (WO) ................ PCT/CN2011/079379

(51) Int. Cl.
| | |
|---|---|
| *A61K 31/428* | (2006.01) |
| *C07D 277/68* | (2006.01) |
| *A61K 45/06* | (2006.01) |
| *A61K 31/167* | (2006.01) |
| *C07C 53/10* | (2006.01) |

(52) U.S. Cl.
CPC .......... *A61K 31/428* (2013.01); *A61K 31/167* (2013.01); *A61K 45/06* (2013.01); *C07C 53/10* (2013.01); *C07D 277/68* (2013.01); *C07B 2200/07* (2013.01)

(58) Field of Classification Search
CPC .... A61K 31/167; A61K 31/428; A61K 45/06; C07D 277/68; C07C 53/10; C07B 2200/07

See application file for complete search history.

(56) References Cited

U.S. PATENT DOCUMENTS

| 7,273,870 B2 | 9/2007 | Frijlink |
| 9,623,012 B2 | 4/2017 | Achour et al. |
| 2006/0189607 A1 | 8/2006 | Bouyssou Thierry |
| 2007/0082918 A1 | 4/2007 | Naftchi |
| 2008/0096940 A1 | 4/2008 | Fairhurst et al. |
| 2015/0336914 A1 | 11/2015 | Cao et al. |

FOREIGN PATENT DOCUMENTS

| EP | 308157 A2 | 3/1989 |
| EP | 0764640 A1 | 3/1997 |
| JP | 2005187357 | 7/2005 |
| WO | 9525104 | 9/1995 |
| WO | 9909018 | 2/1999 |
| WO | 0034248 | 6/2000 |
| WO | 0116108 | 3/2001 |
| WO | 03/072030 A1 | 9/2003 |
| WO | 2004016578 A2 | 2/2004 |

(Continued)

OTHER PUBLICATIONS

Doucet et. al., American Journal of Respiratory and Critical Care Medicine, 2007, American Thoracic Society, 176, 261-269.*
Arnold, N. et al., "The identification of 7-[(R)-2-((1S,2S)-2-benzyloxycyclopentylamino)-1-hydroxyethyl]-4-hydroxybenzothiazolone as an inhaled long-acting B2-adrenoceptor agonist", Bioorganic & Medicinal Chemistry Letters, 24(17):4341-4347, 2014.
Beattie, D. et al., "A physical properties based approach for the exploration of a 4-hydroxybenzothiazolone series of b2-adrenoceptor agonists as inhaled long-acting bronchodilators", Bioorganic & Medicinal Chemistry Letters, 20 (17):5302-5307, 2010.
Stocks, M. et al., "Design driven HtL: The discovery and synthesis of new high efficacy b2-agonists", Bioorganic & Medicinal Chemistry Letters. 21(13):4027-4031, 2011.

(Continued)

*Primary Examiner* — Sarah Pihonak
(74) *Attorney, Agent, or Firm* — Asimina T. Georges Evangelinos

(57) ABSTRACT

The present invention provides a compound of formula (I) in free form or in pharmaceutically acceptable salt form

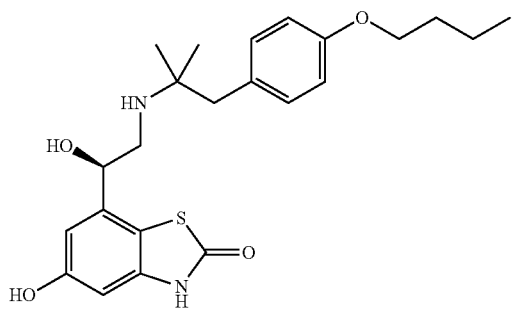

(I)

a method for manufacturing the compound of the invention, and its therapeutic uses. The present invention further provides a combination of pharmacologically active agents and pharmaceutical compositions.

9 Claims, 11 Drawing Sheets

(56) References Cited

FOREIGN PATENT DOCUMENTS

| | | | |
|---|---|---|---|
| WO | 2004016601 A1 | 2/2004 |
| WO | 2004039766 A1 | 5/2004 |
| WO | 2004085058 A1 | 10/2004 |
| WO | 2004087142 A1 | 10/2004 |
| WO | 2004110418 A2 | 12/2004 |
| WO | 2005004846 A1 | 1/2005 |
| WO | 2005004852 A1 | 1/2005 |
| WO | 2005051946 A2 | 6/2005 |
| WO | 2005058299 A1 | 6/2005 |
| WO | 2005074924 A1 | 8/2005 |
| WO | 2005110990 A1 | 11/2005 |
| WO | 2005111002 A2 | 11/2005 |
| WO | 2006014704 A1 | 2/2006 |
| WO | 2006032627 A1 | 3/2006 |
| WO | 2006056471 A1 | 6/2006 |
| WO | 2007027133 A1 | 3/2007 |
| WO | 2007027134 A1 | 3/2007 |
| WO | 2007086078 A2 | 8/2007 |
| WO | 2007091106 A2 | 8/2007 |
| WO | 2007102771 A1 | 9/2007 |
| WO | 2008000483 A2 | 1/2008 |
| WO | 2008075026 A1 | 6/2008 |
| WO | 2009019504 A1 | 2/2009 |
| WO | 2010015792 A1 | 2/2010 |
| WO | 2010019098 A1 | 2/2010 |
| WO | 2010071581 A1 | 6/2010 |
| WO | 2011154678 A1 | 12/2011 |
| WO | 2012156693 A1 | 11/2012 |
| WO | 2013035047 A1 | 3/2013 |
| WO | 2014033654 A1 | 3/2014 |

OTHER PUBLICATIONS

Alcaraz et al. (AstraZeneca), Bioorganic & Medicinal Chemistry Letters, The discovery of new ultra long-acting, vol. 22 (1), pp. 689-695 (2012).
Connolly et al. (AstraZeneca), Bioorganic & Medicinal Chemistry Letters, The discovery of new ultra long-actingâ€, vol. 21(15), pp. 4612-4616 (2011).
Stocks et al., Bioorganic & Medicinal Chemistry Letters, The discovery and Synthesis of new high efficacyâ€, vol. 21 (13), pp. 4027-4031 (2011).
Gould P., International Journal of Pharmaceutics, Salt selection for basic drugs, Elsevier, vol. 33, pp. 201-217 (1986).
Deconinck et al., Pathophysiology of Ducheme Muscularâ€, Pediatric Neurology, Elsevier Inc., vol. 36, pp. 1-7 (2007).
Thompson D.D., Aging and sarcopenia, Journal of Musculoskeletal and Neuronal Interactions, vol. 7, No. 4, pp. 344-345 (2007).
Zeman R.J. et al., Clenbuterol reduces degeneration of exercised or aged dystrophic (mdx) muscle, Muscle and Nerve, vol. 23(4), pp. 521-528 (2000).
Emery P.W. et al., Chronic effects ol 8z-adrenergic agonists on body composition and protein synthesis in the rat, Bioscience Reports. 4, pp. 83-91 (1984).
Gagnon B. et al., A Review of the Drug Treatment of Cachexia Associated with Cancer, Drugs, vol. 55(5), pp. 675-688 (1998).
Argiles J.M. et al., Novel approaches to the treatment of Cachexia, Drug Discovery Today, vol. 13 (1-2), pp. 73-78 (2008).
Pisters P.W.T. et al., Protein and amino acid metabolism in cancer cachexia: Investigative techniques and therapeutic interventions, vol. 30(3), pp. 223-272(1993).
Lynch G. S. et al., Therapeutic approaches for muscle wasting disorders, Pharmacology and Therapeutics, vol. 113 (3), pp. 461-487 (2007).
Lynch G. S., Novel therapies for muscular dystrophy and other muscle wasting conditions, Expert Opinion on Therapeutic Patents, 11(4), pp. 587-601(2001).
Ryall J.G. et al., Attenuation of Age-Related Muscle Wasting and Weakness in Rats After Formoterol Treatment: Therapeutic Implications for Sarcopenia, Journal of Gerontology Series A-Biological Sciences and Medical Sciences, vol. 62(8), pp. 813-823 (2007).
Payan C.A. et al., Periodic Salbutamol in Facioscapulohumeral Muscular Dystrophy: A Randomized Controlled Trial, Archives of Physical Medicine & Rehabilitation, vol. 90 (7), pp. 1094-1101 (2009).
Carbo N. et al., Comparative effects of beta2-adrenergic agonists on muscle waste associated with tumour growth, Cancer Letters, 115(1), pp. 113-118 (1997).
Zeman R. J. et al., Clenbuterol, a beta2-agonist, retards wasting and loss of contractility in irradiated dystrophic mdx Muscle, American Journal of Physiology—Cell Physiology, vol. 267 (3 36-3), pp. C865-C868 (1994).
Stallion A., Anticatabolic effect of the beta2-agonist cimaterol in vivo in tumor-bearing animals, Journal of Surgical Research, vol. 59(3), pp. 387-392 (1995).
Koopman R. et al., The role of b-adrenoceptor signaling in skeletal muscle: therapeutic implications for muscle wasting disorders, Current Opinion in Clinical Nutrition and Metabolic Care, vol. 12 (6), pp. 601-606 (2009).
Skura C.L. et al., Albuterol increases lean body mass in ambulatory boys with Duchenne or Becker muscular dystrophy, Neurology, vol. 70(2), pp. 137-143 (2008).
Van der Kooi E.L. et al., Strength training and albuterol in facioscapulohumeral muscular dystrophy, Neurology, vol. 63 (4), pp. 702-708 (2004).
Kissel J.T. et al., Randomized, double-blind, placebocontrolled trial of albuterol in facioscapulohumeral dystrophy, Neurology, vol. 57(8), pp. 1434-1440 (2001).
Ryall J.G. et al., Systemic administration of b2-adrenoceptor agonists, formoterol and salmeterol, elicit skeletal muscle hypertrophy in rats at micromolar doses, British Journal of Pharmacology, vol. 147(6), pp. 587-595 (2006).
Hayes A. et al., Contractile properties of clenbuterol-treated MDX muscle are enhanced by low-intensity swimming, Journal of Applied Physiology, vol. 82(2), pp. 435-439 (1997).
Busquets S. et al., Anticachectic Effects of Formoterol: A Drug for Potential Treatment of Muscle Wasting, Cancer Research, vol. 64 (18), pp. 6725-6731. (2004).
Baker D.J. et al., Chronic Treatment with the beta 2-Adrenoceptor Agonist Prodrug BRL-47672 Impairs Rat Skeletal Muscle Function by Inducing a Comprehensive Shift to a Faster Muscle Phenotype, The Journal of Pharmacology and Experimental Therapeutics, vol. 319 (1), pp. 439-446 (2006).
Harcourt L.J. et al., Low dose formoterol administration improves muscle function in dystrophic mdx mice without increasing fatigue, Neuromuscular Disorders, vol. 17 (1), pp. 47-55 (2007).
Tillyer et al., Thieme, 3:225-226 (1996).

* cited by examiner

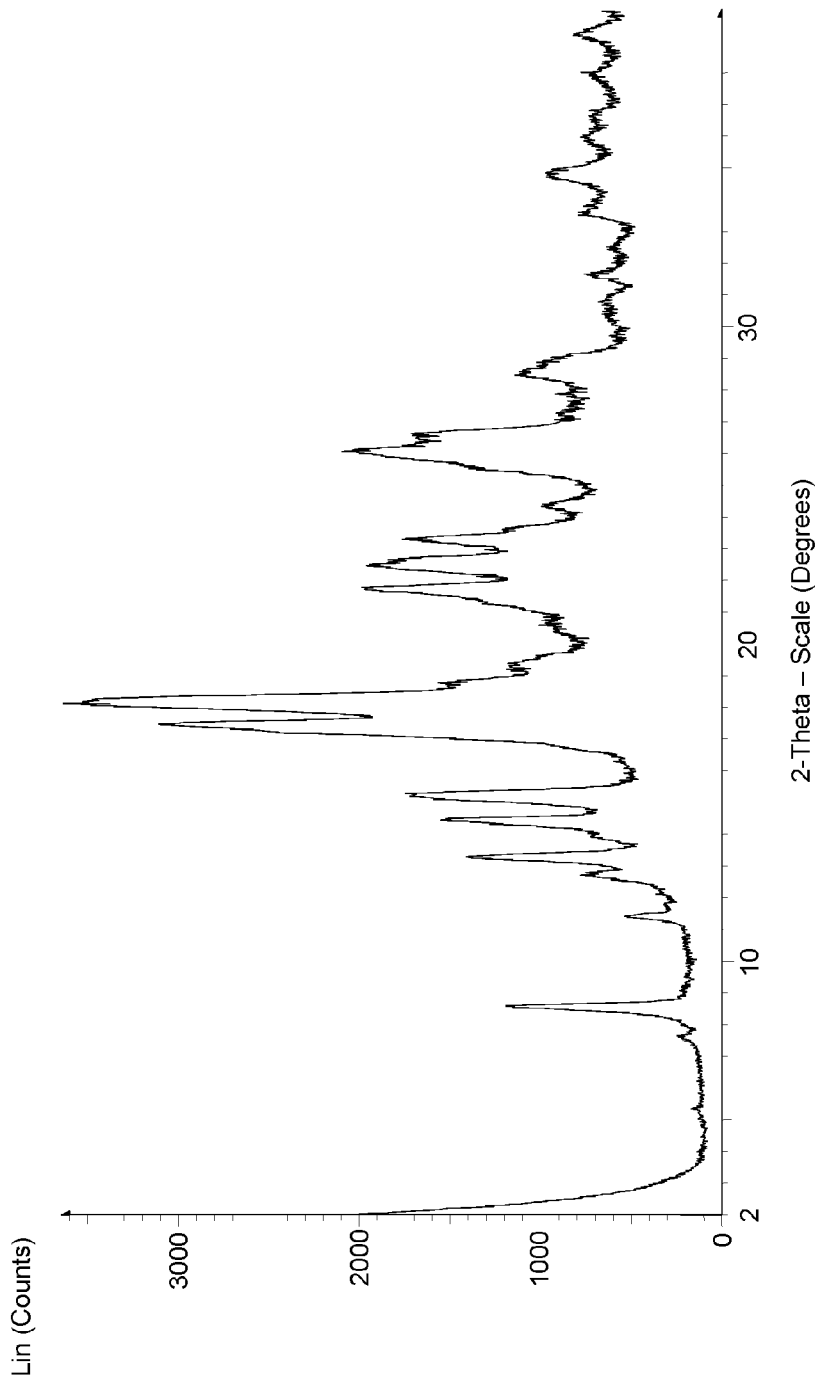

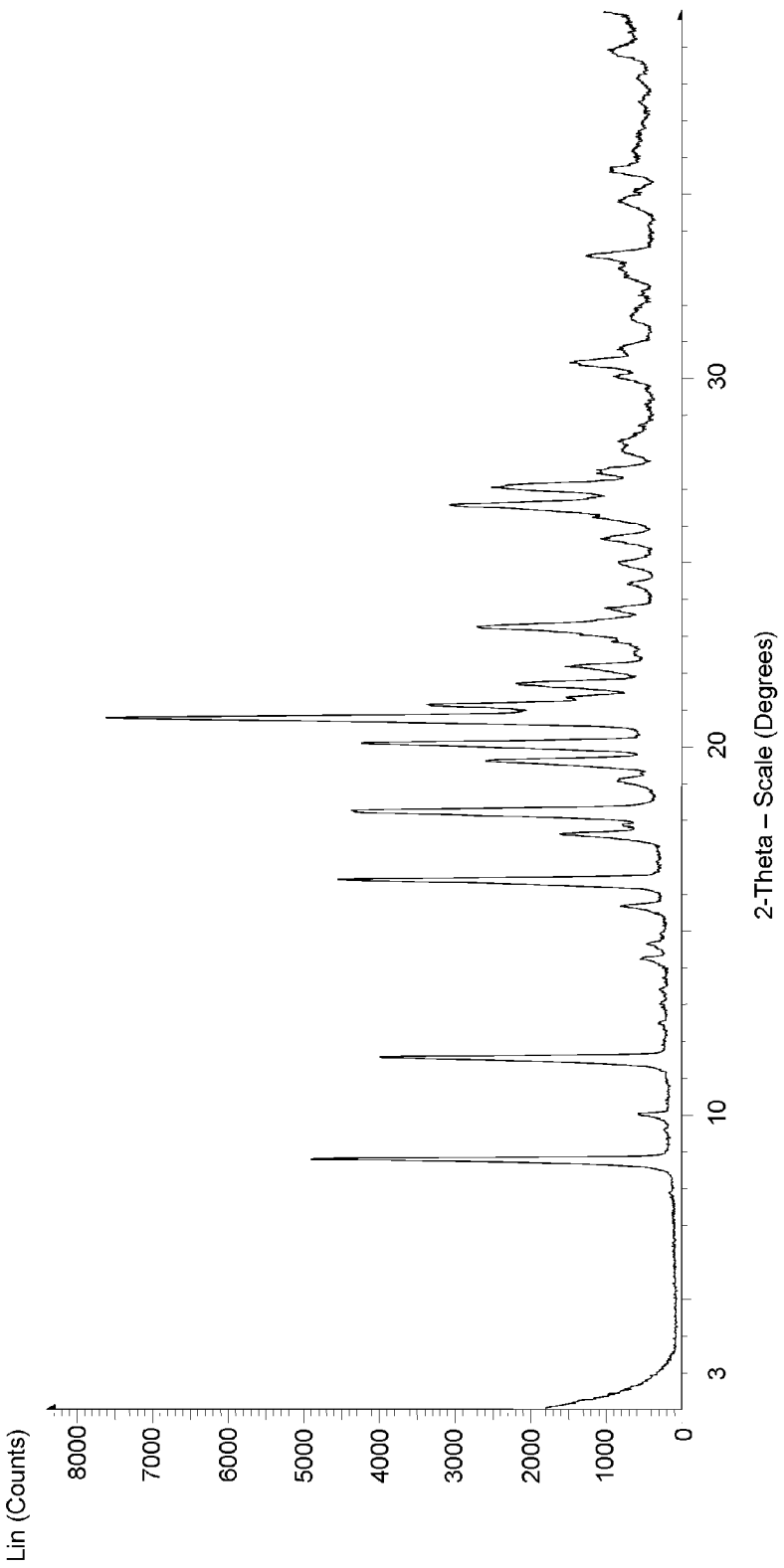

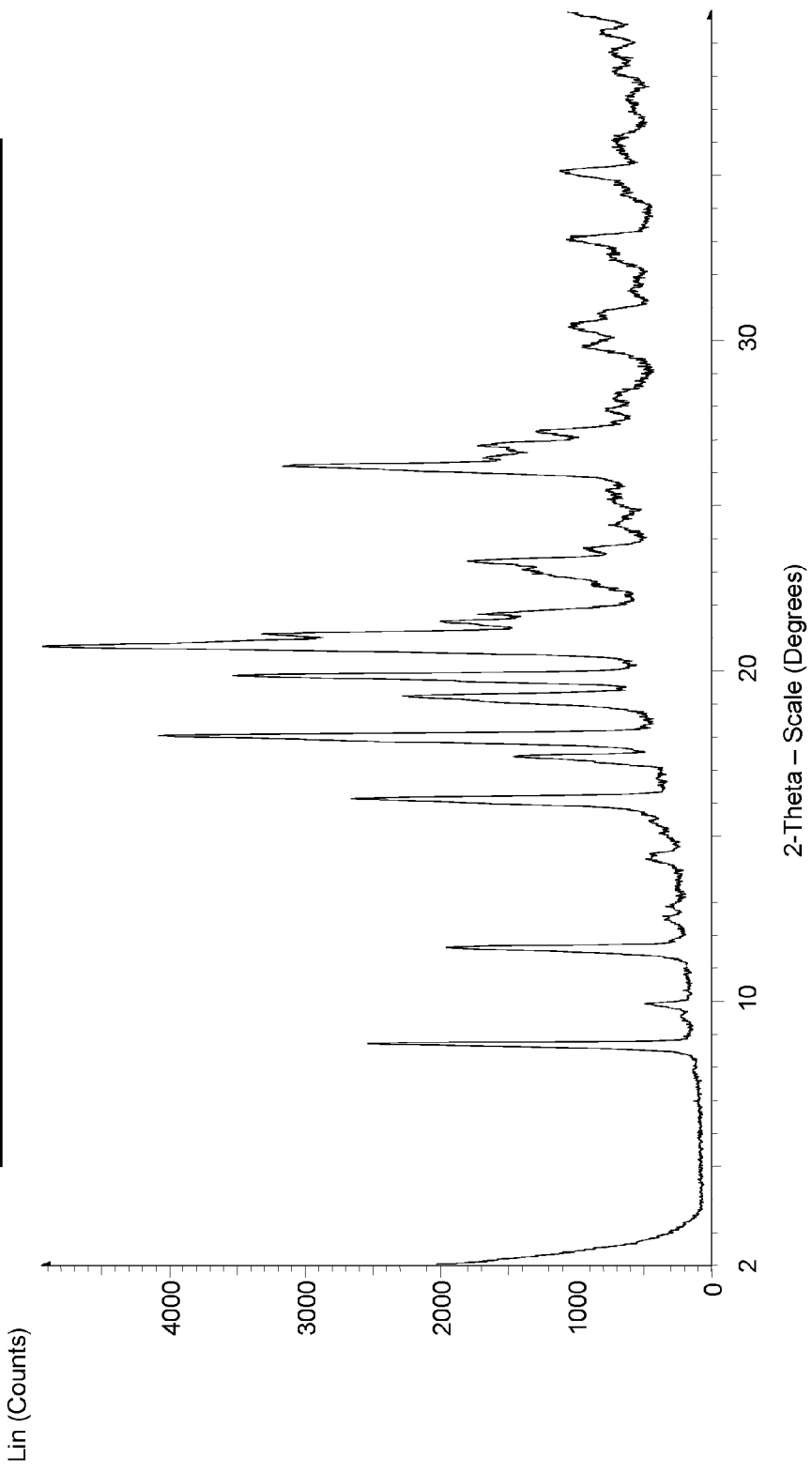

BENZOTHIAZOLONE COMPOUND

The present invention relates to a benzothiazolone compound, to its preparation, to its medical use as a beta-2 adrenoceptor agonist and to medicaments, pharmaceutical compositions and combinations comprising it.

Benzothiazolone compounds which are beta-2-adrenoceptor agonists are described in WO2004/16601 and WO2006/056471. WO2005/110990 also describes benzo-condensed heterocycles as beta-2 agonists.

While beta-2 agonists have long been known for their bronchodilating properties, they are also known for their capability to produce skeletal muscle hypertrophy.

Numerous studies have focused on therapeutic applications of the anabolic properties of beta-2 agonists for ameliorating muscle wasting and improving muscle function. However, this class of compounds has also been associated with undesirable side-effects, including increased risk of adverse cardiovascular-related events. Thus, the use of beta-2 agonists in muscle wasting diseases has hitherto been limited by cardiac hypertrophy and potentially deleterious effects on cardiovascular function.

There is a need to provide new beta-2 agonists that are good drug candidates. In particular, a new beta-2 agonist should bind potently to the beta-2 adrenoceptor whilst showing little affinity for other receptors, such as e.g. the beta-1 adrenoceptor, the alpha-1A adrenoceptor, or the $5HT_{2C}$ receptor, and show functional activity as an agonist. It should be metabolically stable and possess favourable pharmacokinetic properties. It should be non-toxic and demonstrate few side-effects, in particular fewer cardiac side-effects than known marketed beta-2 agonists, such as e.g. formoterol. Furthermore, the ideal drug candidate will exist in a physical form that is stable, non-hygroscopic and easily formulated.

The compound of the invention is a selective beta-2 agonist. In particular, it shows an increased affinity for the beta-2 adrenoceptor which is greater than its affinity for the beta-1 adrenoceptor or the alpha-1A adrenoceptor, compared to known beta-2 agonists such as formoterol. Surprisingly, it also shows a lower affinity for the serotonin receptor ($5HT_{2C}$) and lower functional potency in $5HT_{2C}$ expressing cells than its racemate or its corresponding enantiomer, indicating that it does not affect locomotor activity and food intake which may cause body weight reduction, potentially counteracting beta-2 agonist-induced skeletal muscle hypertrophy. The negative effects of $5HT_{2C}$ receptor agonists on energy intake and body weight are described by J. Halford and J. Harrold in Handb Exp Pharmacol. 2012; (209) 349-56.

The compound of the present invention is therefore potentially useful in the treatment of a wide range of disorders, particularly in the treatment or prevention of muscle-wasting diseases such as muscular dystrophy, disuse-related atrophy, cachexia or sarcopenia.

The treatment of cachexia is also a contemplated use. All forms of cachexia are potentially treatable with the compounds of the present invention, including cancer cachexia for example.

In a first aspect of the invention, there is therefore provided a compound of formula (I) in free form or in pharmaceutically acceptable salt form which is

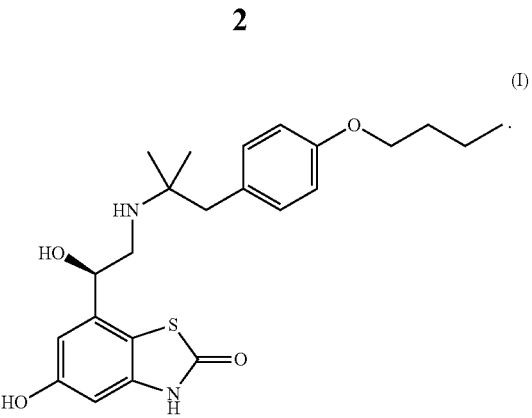

The compound of the invention is (R)-7-(2-(1-(4-butoxyphenyl)-2-methylpropan-2-ylamino)-1-hydroxyethyl)-5-hydroxybenzo[d]thiazol-2(3H)-one.

The following are embodiments of the invention:

Embodiment 1

A compound according to the first aspect of the invention.

Embodiment 2

A compound according to embodiment 1 which is (R)-7-(2-(1-(4-butoxyphenyl)-2-methylpropan-2-ylamino)-1-hydroxyethyl)-5-hydroxybenzo[d]thiazol-2(3H)-one in free form.

Embodiment 3

A compound according embodiment 1 which is (R)-7-(2-(1-(4-butoxyphenyl)-2-methylpropan-2-ylamino)-1-hydroxyethyl)-5-hydroxybenzo[d]thiazol-2(3H)-one in acetate salt form.

Embodiment 4

A compound according to embodiment 1 which is (R)-7-(2-(1-(4-butoxyphenyl)-2-methylpropan-2-ylamino)-1-hydroxyethyl)-5-hydroxybenzo[d]thiazol-2(3H)-one in glycolate salt form.

Embodiment 5

A pharmaceutical composition comprising a therapeutically effective amount of a compound according to any one of embodiments 1 to 4 and one or more pharmaceutically acceptable carriers.

Embodiment 6

A pharmaceutical composition according to embodiment 5 wherein one of the pharmaceutically acceptable carriers is benzyl alcohol.

Embodiment 7

A combination comprising a therapeutically effective amount of a compound according to any one of embodiments 1 to 4 and one or more therapeutically active co-agents.

Embodiment 8

A method of treatment or prevention of muscular dystrophy, disuse-related atrophy, cachexia or sarcopenia comprising administering a therapeutically effective amount of a compound according to any one of embodiments 1 to 4 to a subject in need thereof.

Embodiment 9

A method according to embodiment 8, wherein the compound is administered by subcutaneous infusion or injection.

Embodiment 10

A compound according to according to any one of embodiments 1 to 4 for use as a medicament.

Embodiment 11

A compound according to any one of embodiments 1 to 4 for use in the treatment or prevention of muscular dystrophy, disuse-related atrophy, cachexia or sarcopenia.

Embodiment 12

Use of a compound according to any one of embodiments 1 to 4 in the manufacture of a medicament for the treatment or prevention of muscular dystrophy, disuse-related atrophy, cachexia or sarcopenia.

Embodiment 13

A process for the manufacture of a compound of formula (I) in free form or in pharmaceutically acceptable salt form which includes the steps of:
a) the reaction of a compound of formula (IIa) in free form or in pharmaceutically acceptable salt form

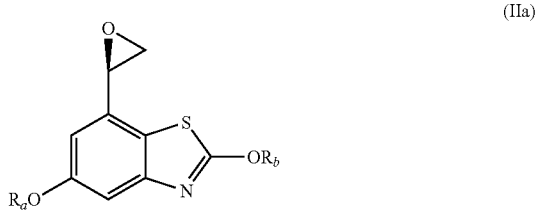

(IIa)

in which $R_a$ and $R_b$ are protecting groups with 2-(4-butoxy-phenyl)-1,1-dimethyl-ethylamine;
b) the cleavage of protecting groups optionally present;
c) the recovery of the so obtainable compound of formula (I) in free form or in pharmaceutically acceptable salt form.

Embodiment 14

A process for the manufacture of a compound of formula (I) in free form or in pharmaceutically acceptable salt form according to embodiment 13 in which compound (IIa) is obtained by the reaction of a compound of formula (IIIa) in free form or in pharmaceutically acceptable salt form

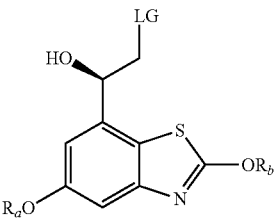

(IIIa)

in which in which $R_a$ and $R_b$ are protecting groups and LG is a leaving group with a base and optionally a phase transfer catalyst.

Embodiment 15

A process according to embodiment 14, wherein the base is potassium carbonate.

Embodiment 16

A process according to embodiment 14, wherein the base is sodium hydroxide.

Embodiment 17

A process according to any of embodiments 14 to 16, wherein the phase transfer catalyst is tetra-butylammonium iodide.

Embodiment 18

A process for the manufacture of a compound of formula (I) in free form or in pharmaceutically acceptable salt form according to embodiments 14 to 17 in which compound (IIIa) is obtained by the stereoselective reduction of a compound of formula (IVa-2) in free form or in pharmaceutically acceptable salt form

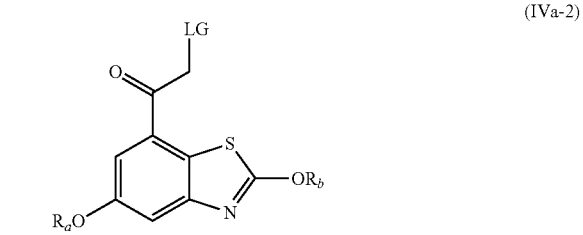

(IVa-2)

in which $R_a$ and $R_b$ are protecting groups and LG is a leaving group.

Embodiment 19

A process according to embodiment 18 wherein the stereoselective reduction is carried out with [N-[(1S,2S)-2-(Amino-κN)-1,2-diphenylethyl]-4-methylbenzenesulfonamidato-κN]chloro[(1,2,3,4,5,64)-1-methyl-4-(1-methylethyl)benzene]-ruthenium (RuCl(p-cymene)[(S,S)-Ts-DPEN]).

Embodiment 20

A process according to embodiment 18 or 19 wherein LG is chloro.

Embodiment 21

A process according to embodiment 20 in which compound (IVa'-2) in free form or in pharmaceutically acceptable salt form

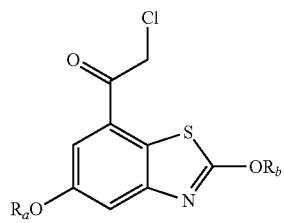
(IVa'-2)

is obtained by the reaction of a compound of formula (Va) in free form or in pharmaceutically acceptable salt form

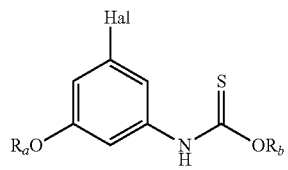
(Va)

in which $R_a$ and $R_b$ are protecting groups and Hal is a halogen with 2-chloro-N-methoxy-N-methyl-acetamide in the presence of a strong base.

Embodiment 22

A process according to embodiment 21, wherein the strong base is tert-butyllithium.

Embodiment 23

A process for the manufacture of a compound of formula (I) in free form or in pharmaceutically acceptable salt form which includes the steps of:
a) the reaction of a compound of formula (IIIa) in free form or in pharmaceutically acceptable salt form

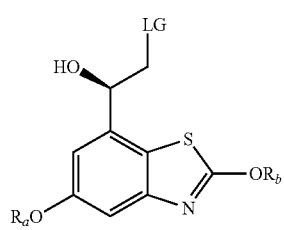
(IIIa)

in which $R_a$ and $R_b$ are protecting groups and LG is a leaving group with 2-(4-butoxy-phenyl)-1,1-dimethyl-ethylamine;

b) the cleavage of any protecting groups still present;

c) the recovery of the so obtainable compound of formula (I) in free form or in pharmaceutically acceptable salt form.

Embodiment 24

A process according to embodiment 23, wherein LG is chloro or p-toluenesulfonyl.

EMBODIMENT 25

A process according to any of embodiments 13 to 24 wherein $R_a$ is tert-butyl.

Embodiment 26

A process according to any of embodiments 13 to 25, wherein $R_b$ is isopropyl.

Embodiment 27

A compound of formula (Ia) in free form or in pharmaceutically acceptable salt form

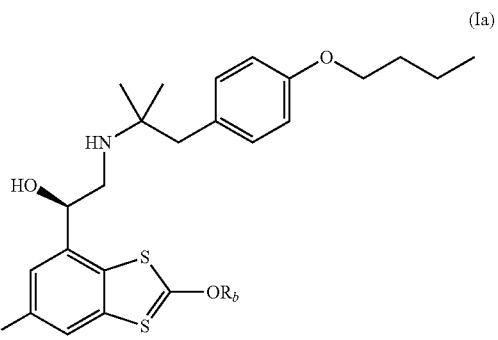
(Ia)

in which $R_a$ and $R_b$ are protecting groups.

Embodiment 28

A compound of formula (IIa) in free form or pharmaceutically acceptable salt form

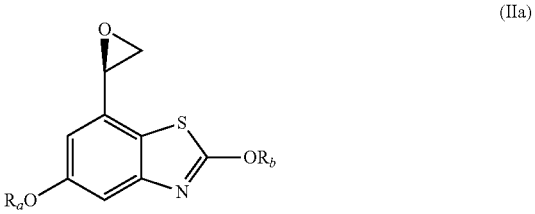
(IIa)

in which $R_a$ and $R_b$ are protecting groups.

Embodiment 29

A compound of formula (IIIa-2) in free form or pharmaceutically acceptable salt form

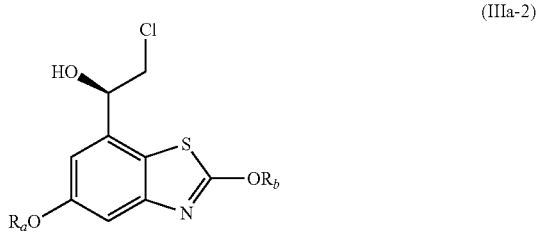

(IIIa-2)

in which $R_a$ and $R_b$ are protecting groups.

Embodiment 30

A compound of formula (IVa-2) in free form or pharmaceutically acceptable salt form

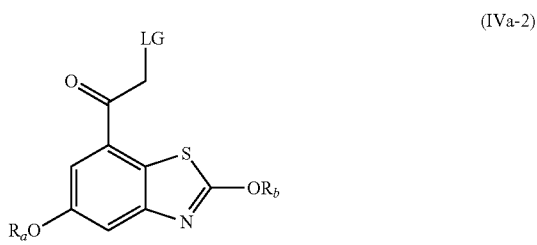

(IVa-2)

in which $R_a$ and $R_b$ are protecting groups and LG is a leaving group.

Embodiment 31

A compound according to embodiment 30, wherein LG is chloro.

Embodiment 32

A compound according to any of embodiments 27 to 31, wherein $R_a$ is tert-butyl.

Embodiment 33

A compound according to any of embodiments 27 to 32, wherein $R_b$ is isopropyl.

BRIEF DESCRIPTION OF FIGURES

FIG. 5 shows the X-ray powder diffraction pattern of crystalline free base Compound A (compound of the invention).

FIG. 6 shows the X-ray powder diffraction pattern of the crystalline acetate salt of Compound A (compound of the invention).

FIG. 7 shows the X-ray powder diffraction pattern of the crystalline glycolate salt of Compound A (compound of the invention).

Figure 1:
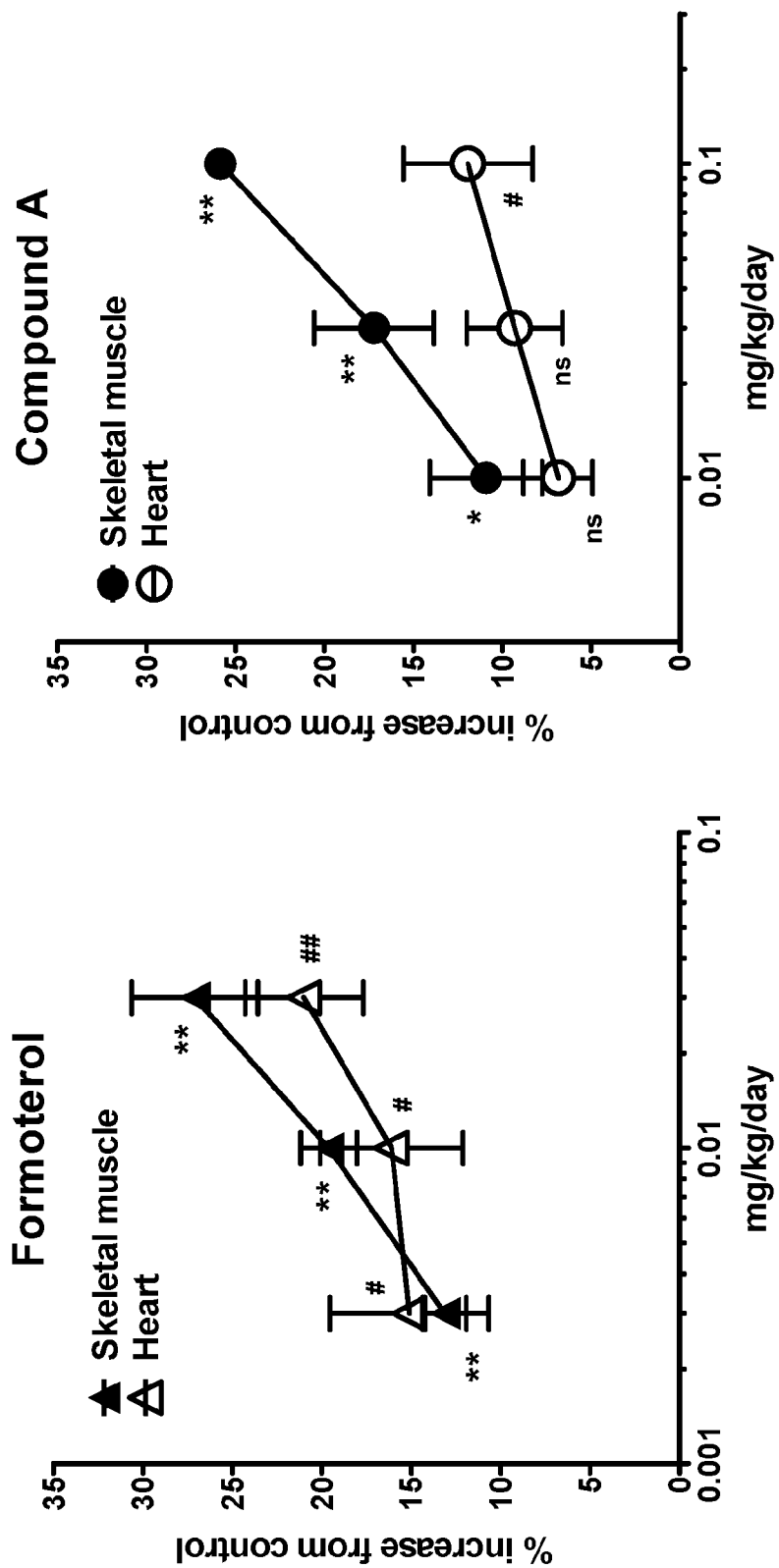
FIG. 1 shows the skeletal muscle mass and heart mass increase in rats injected with formoterol vs compound A (compound of the invention)–(values are expressed as means±SEM (n=5-6); pool of skeletal muscles (gastrocnemius-soleus-tibialis) normalized by initial body weight; heart weight normalized by brain weight.

Unless specified otherwise, the term "compound of the present invention", "compound of the invention" or "compound A" refers to the compound of formula (I), salts of the compound, hydrates or solvates of the compound or salts, as well as tautomers and isotopically labeled compounds (including deuterium substitutions). The compound of the present invention further comprises polymorphs of the compound of formula (I) and salts thereof.

As used herein, the term "halogen" or "halo" refers to fluoro, chloro, bromo, and iodo.

As used herein, the absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line.

Any asymmetric atom (e.g., carbon or the like) of a compound can be present in racemic or enantiomerically enriched, for example the (R)-, (S)- or (R,S)-configuration. The racemic 50:50 mixture of stereoisomers is designated as (R,S) and enantiomerically enriched forms by the enantiomeric excess of (R) to (S) respectively or (S) to (R) forms. The enantiomeric excess is represented usually by the equation ee=((m1−m2)/(m1+m2))*100% where m1 and m2 represent the mass of the respective enatiomeric forms R and S.

The compound of the present invention contains one asymmetric centre which is defined in terms of absolute stereochemistry as (R). Its corresponding enantiomer is defined as (S) which is the less active form.

In certain embodiments of the invention, the asymmetric atom has at least 95, 98 or 99 enantiomeric excess in the (R)-configuration.

Thus in one embodiment of the invention, there is provided (R)-7-(2-(1-(4-butoxyphenyl)-2-methylpropan-2-ylamino)-1-hydroxyethyl)-5-hydroxybenzo[d]thiazol-2 (3H)-one, or a pharmaceutically acceptable salt thereof (for example an acetate or glycolate salt thereof), in at least 95% enantiomeric excess.

In another embodiment of the invention, there is provided (R)-7-(2-(1-(4-butoxyphenyl)-2-methylpropan-2-ylamino)-1-hydroxyethyl)-5-hydroxybenzo[d]thiazol-2(3H)-one, or a pharmaceutically acceptable salt thereof (for example an acetate or glycolate salt thereof), in at least 98% enantiomeric excess.

In yet another embodiment of the invention, there is provided (R)-7-(2-(1-(4-butoxyphenyl)-2-methylpropan-2-ylamino)-1-hydroxyethyl)-5-hydroxybenzo[d]thiazol-2

(3H)-one, or a pharmaceutically acceptable salt thereof (for example an acetate or glycolate salt thereof), in at least 99% enantiomeric excess.

In one embodiment of the invention, there is provided a pharmaceutical composition comprising a therapeutically effective amount of (R)-7-(2-(1-(4-butoxyphenyl)-2-methylpropan-2-ylamino)-1-hydroxyethyl)-5-hydroxybenzo[d]thiazol-2(3H)-one, or a pharmaceutically acceptable salt thereof (for example an acetate or glycolate salt thereof), and one or more pharmaceutically acceptable carriers wherein the (R)-7-(2-(1-(4-butoxyphenyl)-2-methylpropan-2-ylamino)-1-hydroxyethyl)-5-hydroxybenzo[d]thiazol-2 (3H)-one, or pharmaceutically acceptable salt thereof, is present in at least 95% enantiomeric excess.

In another embodiment of the invention, there is provided a pharmaceutical composition comprising a therapeutically effective amount of (R)-7-(2-(1-(4-butoxyphenyl)-2-methylpropan-2-ylamino)-1-hydroxyethyl)-5-hydroxybenzo[d]thiazol-2(3H)-one, or a pharmaceutically acceptable salt thereof (for example an acetate or glycolate salt thereof), and one or more pharmaceutically acceptable carriers wherein the (R)-7-(2-(1-(4-butoxyphenyl)-2-methylpropan-2-ylamino)-1-hydroxyethyl)-5-hydroxybenzo[d]thiazol-2 (3H)-one, or pharmaceutically acceptable salt thereof, is present in at least 98% enantiomeric excess.

In yet another embodiment of the invention, there is provided a pharmaceutical composition comprising a therapeutically effective amount of (R)-7-(2-(1-(4-butoxyphenyl)-2-methylpropan-2-ylamino)-1-hydroxyethyl)-5-hydroxybenzo[d]thiazol-2(3H)-one, or a pharmaceutically acceptable salt thereof (for example an acetate or glycolate salt thereof), and one or more pharmaceutically acceptable carriers wherein the (R)-7-(2-(1-(4-butoxyphenyl)-2-methylpropan-2-ylamino)-1-hydroxyethyl)-5-hydroxybenzo[d]thiazol-2(3H)-one, or pharmaceutically acceptable salt thereof, is present in at least 99% enantiomeric excess.

The compound of the present invention contains one asymmetric centre which is defined in terms of absolute stereochemistry as (R). Its corresponding enantiomer is defined as (S).

Depending on the choice of the starting materials and procedures for the chemical synthesis, compounds can be present in the form of one of the possible isomers or as mixtures thereof, for example as pure optical isomers, or as isomer mixtures, such as racemates. Optically active (R)- and (S)-isomers may be prepared using chiral synthons or chiral reagents, or resolved using conventional techniques. All tautomeric forms of the compound of the present invention are intended to be included.

Accordingly, as used herein the compound of the present invention can be in the form of tautomers or mixtures thereof.

Any resulting racemates of final products or synthesis intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compound of the present invention into its optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic or enantiomerically enriched products can also be resolved by chiral chromatography, e.g., high pressure liquid chromatography (HPLC) using a chiral adsorbent.

As used herein, the terms "salt" or "salts" refers to an acid addition or base addition salt of the compound of the invention. "Salts" include in particular "pharmaceutically acceptable salts". The term "pharmaceutically acceptable salts" refers to salts that retain the biological effectiveness and properties of the compound of this invention and, which typically are not biologically or otherwise undesirable. The compound of formula I of the present invention is capable of forming a characteristic salt with a defined acid by virtue of the presence of a basic amino group in the side chain. It is also capable to form characteristic salts with defined bases by virtue of the presence of two acidic groups (phenol; thiazolone ring) in the heterocylic moiety.

Pharmaceutically acceptable acid addition salts may be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, glycolic, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

In one embodiment of the invention, there is provided (R)-7-(2-(1-(4-butoxyphenyl)-2-methylpropan-2-ylamino)-1-hydroxyethyl)-5-hydroxybenzo[d]thiazol-2(3H)-one in acetate, benzoate, camphorate, fumarate, glycolate, lactate, malonate, mesylate, succinate, sulfate, tartrate or xinafoate salt form.

In one particular embodiment of the invention, there is provided (R)-7-(2-(1-(4-butoxyphenyl)-2-methylpropan-2-ylamino)-1-hydroxyethyl)-5-hydroxybenzo[d]thiazol-2 (3H)-one in acetate salt form.

In another particular embodiment of the invention, there is provided (R)-7-(2-(1-(4-butoxyphenyl)-2-methylpropan-2-ylamino)-1-hydroxyethyl)-5-hydroxybenzo[d]thiazol-2 (3H)-one in glycolate salt form.

Inorganic acids from which salts may be derived include, for example, hydrochloric acid, hydrobromic acid, sulfuric acid, nitric acid, phosphoric acid, and the like.

Organic acids from which salts may be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts may be formed with inorganic and organic bases.

Inorganic bases from which salts may be derived include, for example, ammonium salts and metals from columns I to XII of the periodic table. In certain embodiments, the salts are derived from sodium, potassium, ammonium, calcium, magnesium and iron; particularly suitable salts include ammonium, potassium, sodium, calcium and magnesium salts.

Organic bases from which salts may be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of the compound with a stoichiometric amount of the appropriate base (such as Na, Ca, Mg, or K hydroxide, carbonate, bicarbonate or the like), or by reacting free base forms of the compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, $2^{nd}$ revised edition, 2011).

Furthermore, the compound of the present invention, including its salts, may also be obtained in the form of its hydrates, or include other solvents used for its crystallization. The compound of the present invention may inherently or by design form solvates with pharmaceutically acceptable solvents (including water); therefore, it is intended that the invention embrace both solvated and unsolvated forms. The term "solvate" refers to a molecular complex of the compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compound of the present invention, including salts, hydrates and solvates thereof, may inherently or by design form polymorphs.

In one embodiment of the invention, there is provided (R)-7-(2-(1-(4-butoxyphenyl)-2-methylpropan-2-ylamino)-1-hydroxyethyl)-5-hydroxybenzo[d]thiazol-2(3H)-one in crystalline form.

In another embodiment of the invention, there is provided (R)-7-(2-(1-(4-butoxyphenyl)-2-methylpropan-2-ylamino)-1-hydroxyethyl)-5-hydroxybenzo[d]thiazol-2(3H)-one acetate salt in crystalline form.

In yet another embodiment of the invention, there is provided (R)-7-(2-(1-(4-butoxyphenyl)-2-methylpropan-2-ylamino)-1-hydroxyethyl)-5-hydroxybenzo[d]thiazol-2(3H)-one glycolate salt in crystalline form.

In one embodiment of the invention, there is provided crystalline (R)-7-(2-(1-(4-butoxyphenyl)-2-methylpropan-2-ylamino)-1-hydroxyethyl)-5-hydroxybenzo[d]thiazol-2(3H)-one in substantially pure form.

In another embodiment of the invention, there is provided crystalline (R)-7-(2-(1-(4-butoxyphenyl)-2-methylpropan-2-ylamino)-1-hydroxyethyl)-5-hydroxybenzo[d]thiazol-2(3H)-one acetate salt in substantially pure form.

In yet another embodiment of the invention, there is provided crystalline (R)-7-(2-(1-(4-butoxyphenyl)-2-methylpropan-2-ylamino)-1-hydroxyethyl)-5-hydroxybenzo[d]thiazol-2(3H)-one glycolate salt in substantially pure form.

As used herein, "substantially pure," when used in reference to crystalline (R)-7-(2-(1-(4-butoxyphenyl)-2-methylpropan-2-ylamino)-1-hydroxyethyl)-5-hydroxybenzo[d]thiazol-2(3H)-one, or its pharmaceutically acceptable salt, means having a purity greater than 90 weight %, including greater than 90, 91, 92, 93, 94, 95, 96, 97, 98, and 99 weight %, and also including equal to about 100 weight % of (R)-7-(2-(1-(4-butoxyphenyl)-2-methylpropan-2-ylamino)-1-hydroxyethyl)-5-hydroxybenzo[d]thiazol-2(3H)-one, based on the weight of the compound, or its pharmaceutically acceptable salt.

The presence of reaction impurities and/or processing impurities may be determined by analytical techniques known in the art, such as, for example, chromatography, nuclear magnetic resonance spectroscopy, mass spectrometry, or infrared spectroscopy.

In a more focused aspect, the invention relates to a crystalline form of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with at least one, two or three peaks having angle of refraction 2 theta (θ) values selected from 8.5, 13.3, 13.9, 14.4, 15.2, 17.2, 17.5, 18.1, 21.3 and 22.5° when measured using CuK$_\alpha$ radiation, more particularly wherein said values are plus or minus 0.2° 2θ.

In one embodiment, the invention relates to a crystalline form of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 15.2° when measured using CuK$_\alpha$ radiation, more particularly wherein said value is plus or minus 0.2° 2θ.

In one embodiment, the invention relates to a crystalline form of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 18.1° when measured using CuK$_\alpha$ radiation, more particularly wherein said value is plus or minus 0.2° 2θ.

In one embodiment, the invention relates to a crystalline form of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 22.5° when measured using CuK$_\alpha$ radiation, more particularly wherein said value is plus or minus 0.2° 2θ.

In one embodiment, the invention relates to a crystalline form of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern substantially the same as the X-ray powder diffraction pattern shown in FIG. 5 when measured using CuK$_\alpha$ radiation. For details see Example 5.

In another aspect, the invention relates to a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with at least one, two or three peaks having angle of refraction 2 theta (θ) values selected from 8.8, 11.5, 16.4, 17.6, 18.2, 19.6, 20.1, 20.8, and 21.1° when measured using CuK$_\alpha$ radiation, more particularly wherein said values are plus or minus 0.2° 2θ.

In one embodiment, the invention relates to a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 8.8° when measured using CuK$_\alpha$ radiation, more particularly wherein said value is plus or minus 0.2° 2θ.

In one embodiment, the invention relates to a crystalline form of the acetate salt of (R)-7-(2-(1-(4-butoxyphenyl)-2-methylpropan-2-ylamino)-1-hydroxyethyl)-5-hydroxybenzo[d]thiazol-2(3H)-one which has an X-ray powder diffraction pattern with a peak at an angle of refraction 2θ value of 16.4° when measured using CuK$_\alpha$ radiation, more particularly wherein said value is plus or minus 0.2° 2θ.

In one embodiment, the invention relates to a crystalline form of the acetate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern with a peak at an angle of refraction 2θ value of 20.8° when measured using CuK$_\alpha$ radiation, more particularly wherein said value is plus or minus 0.2° 2θ.

In one embodiment, the invention relates to a crystalline form of the acetate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern substantially the same as the X-ray powder diffraction pattern shown in FIG. 6 when measured using CuK$_\alpha$ radiation. For details see Example 6.

In yet another aspect, the invention relates to a crystalline form of the glycolate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern with at least one, two or three peaks having angle of refraction 2 theta (θ) values selected from 8.7, 11.6, 16.1, 18.0, 19.8, 20.7, and 21.1° when measured using CuK$_\alpha$ radiation, more particularly wherein said values are plus or minus 0.2° 2θ.

In one embodiment, the invention relates to a crystalline form of the glycolate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern with a peak at an angle of refraction 2θ value of 18.0° when measured using CuK$_\alpha$ radiation, more particularly wherein said value is plus or minus 0.2° 2θ.

In one embodiment, the invention relates to a crystalline form of the glycolate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern with a peak at an angle of refraction 2θ value of 19.8° when measured using CuK$_\alpha$ radiation, more particularly wherein said value is plus or minus 0.2° 2θ.

In one embodiment, the invention relates to a crystalline form of the glycolate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern with a peak at an angle of refraction 2θ value of 20.7° when measured using CuK$_\alpha$ radiation, more particularly wherein said value is plus or minus 0.2° 2θ.

In one embodiment, the invention relates to a crystalline form of the glycolate salt of (R)-7-(2-(1-(4-butoxyphenyl)-2-methylpropan-2-ylamino)-1-hydroxyethyl)-5-hydroxy-benzo[d]thiazol-2(3H)-one which has an X-ray powder diffraction pattern substantially the same as the X-ray powder diffraction pattern shown in FIG. 7 when measured using CuK$_\alpha$ radiation. For details see Example 7.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

One of ordinary skill in the art will also appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention is not limited to the crystal form that provides an X-ray diffraction pattern completely identical to the X-ray diffraction pattern depicted in the accompanying FIGS. 5, 6 and 7 disclosed herein. Any crystal forms that provide X-ray diffraction patterns substantially identical to those disclosed in the accompanying FIGS. 5, 6 and 7 fall within the scope of the present invention. The ability to ascertain substantial identities of X-ray diffraction patterns is within the purview of one of ordinary skill in the art.

Pharmaceutically acceptable solvates in accordance with the invention include those wherein the solvent of crystallization may be isotopically substituted, e.g. $D_2O$, $d_6$-acetone, $d_6$-DMSO.

The formula given herein is also intended to represent unlabeled forms as well as isotopically labeled forms of the compound. An isotopically labeled compound of the invention has a structure depicted by the formula given herein except that one or more atoms are replaced by an atom having a selected atomic mass or mass number. Examples of isotopes that can be incorporated into the compound of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. An isotopically-labeled compound of formula (I) can generally be prepared by conventional techniques known to those skilled in the art or by processes analogous to those described in the accompanying Examples using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in the compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The compound of the invention may be capable of forming co-crystals with suitable co-crystal formers. These co-crystals may be prepared from a compound of formula (I) by known co-crystal forming procedures. Such procedures include grinding, heating, co-subliming, co-melting, or contacting in solution a compound of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of the compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease associated with beta-2-adrenoceptor activity; or (2) increasing or promoting the activity of beta-2-adrenoceptor.

In another non-limiting embodiment, the term "a therapeutically effective amount" refers to the amount of the compound of the present invention that, when administered to a cell, or a tissue, or a non-cellular biological material, or a medium, is effective to at least partially increase or promote the activity of beta-2-adrenoceptor. The meaning of the term "a therapeutically effective amount" as illustrated in the above embodiment for beta-2-adrenoceptor also applies by the same means to any other relevant proteins/peptides/enzymes, such as IGF-1 mimetics or ActRIIB/myostatin blockers and the like.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illustrate the invention and does not pose a limitation on the scope of the invention otherwise claimed.

The compound of formula (I) can be prepared according to the Scheme provided infra.

Scheme 1

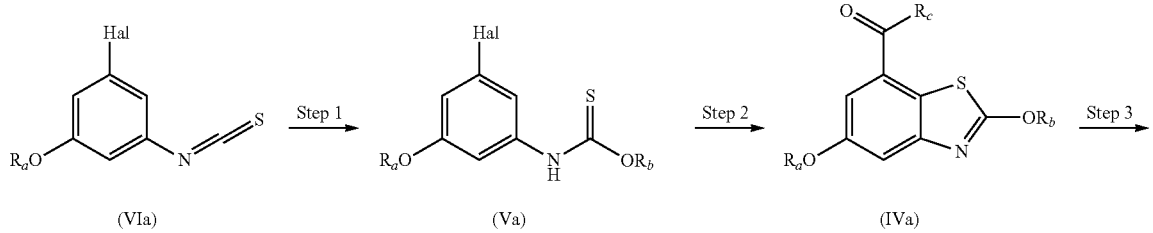

(VIa)     (Va)     (IVa)

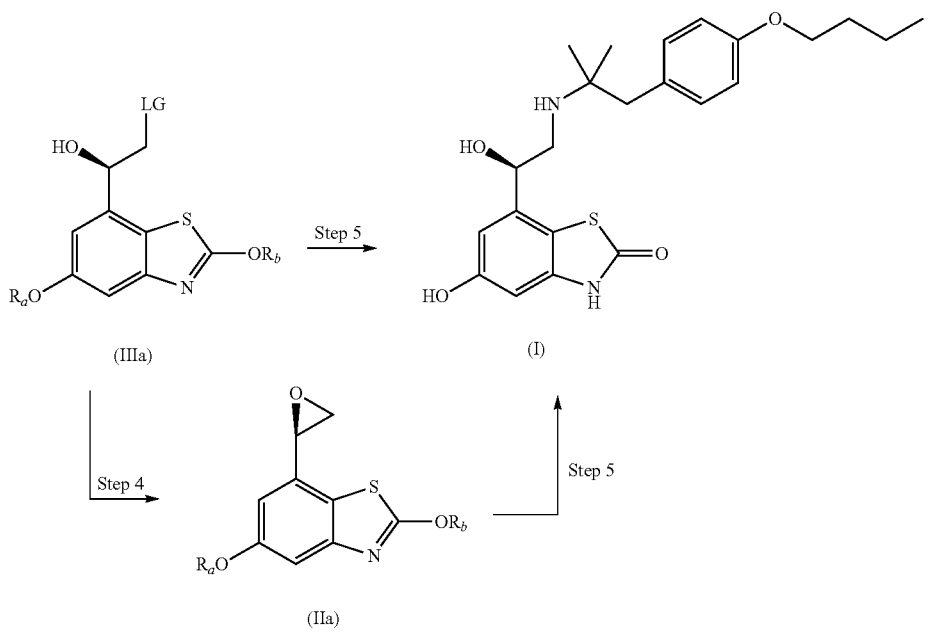

(IIIa)   (I)

(IIa)

The process steps are described in more details below.

Step 1: A compound of formula (VIa) wherein Hal represents halogen and $R_a$ is a protecting group is reacted with a compound of formula $R_bOH$ wherein $R_b$ is a protecting group in the presence of a suitable base, e.g. triethylamine, to give a compound of formula (Va) wherein Hal represents halogen and $R_a$ and $R_b$ are protecting groups.

Step 2: A compound of formula (Va) is reacted with a suitable strong base, e.g. tert-butyllithium, in a suitable solvent, e.g. tetrahydrofuran (THF) in the presence of a suitable carbonylating agent, e.g. a suitable amide, to give a compound of formula (IVa) wherein $R_a$ and $R_b$ are protecting groups and $R_b$ is hydrogen or any moiety derived from the carbonylating agent.

Step 3: A compound of formula (IVa) is optionally functionalised prior to stereoselective conversion to give a compound of formula (IIIa) wherein $R_a$ and $R_b$ are protecting groups and LG is a leaving group.

Step 4: A compound of formula (IIIa) is treated with a suitable base, e.g. sodium bicarbonate, to give a compound of formula (IIa) wherein $R_a$ and $R_b$ are protecting groups.

Step 5: A compound of formula (IIa) or (IIIa) is reacted with 2-(4-butoxy-phenyl)-1,1-dimethyl-ethylamine in a suitable solvent e.g. toluene, optionally in the presence of a suitable base, e.g. potassium carbonate, followed by deprotection in the presence of a suitable acid, e.g. hydrochloric acid, to give a compound of formula (I).

In a further aspect, the invention relates to a process for the preparation of a compound of formula (I), in free from or in pharmaceutically acceptable salt form, comprising a) the reaction of a compound of formula (IIa) in free form or in pharmaceutically acceptable salt form

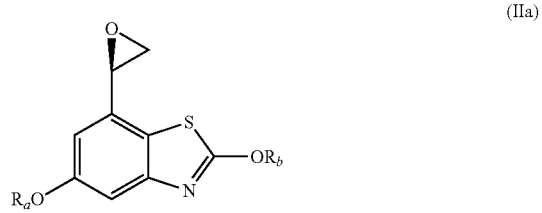

(IIa)

in which $R_a$ and $R_b$ are protecting groups with 2-(4-butoxy-phenyl)-1,1-dimethyl-ethylamine;
b) the cleavage of any protecting groups still present;
c) the recovery of the so obtainable compound of formula (I) in free form or in pharmaceutically acceptable salt form.

In a further aspect, the invention relates to a process for the manufacture of a compound of formula (I) in free form or in pharmaceutically acceptable salt form which includes the steps of:

a) the reaction of a compound of formula (IIIa) in free form or in pharmaceutically acceptable salt form

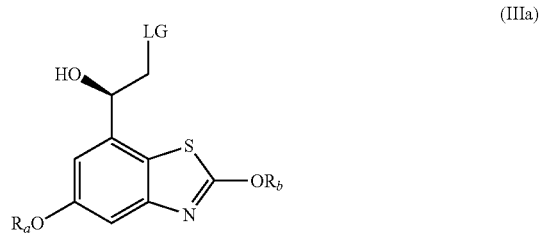

(IIIa)

in which $R_a$ and $R_b$ are protecting groups and LG is a leaving group with 2-(4-butoxy-phenyl)-1,1-dimethyl-ethylamine;

b) the cleavage of any protecting groups still present;
c) the recovery of the so obtainable compound of formula (I) in free form or in pharmaceutically acceptable salt form.

In another aspect, the invention relates to a process for the preparation of a compound of formula (IIIa), in free from or in pharmaceutically acceptable salt form,

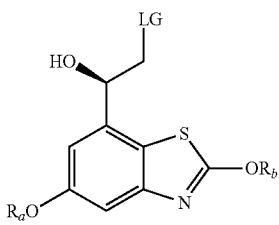

(IIIa)

comprising the stereoselective reduction of a compound of formula (IVa-2) in free form or in pharmaceutically acceptable salt form

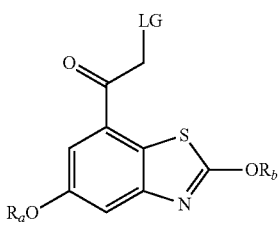

(IVa-2)

in which $R_a$ and $R_b$ are protecting groups and LG is a leaving group to give a compound of formula (IIIa) in free form or in pharmaceutically acceptable salt form.

In the processes of the invention, typical protecting groups include isopropyl, tert-butyl, tert-butyldimethylsilyl.

In the processes of the invention, typical leaving groups include chloride, p-toluenesulfonyl, bromide, methanesulfonyl, benzenesulfonyl, iodide.

The reactions can be effected according to conventional methods, for example as described in the Examples. The work-up of the reaction mixtures and the purification of the compounds thus obtainable may be carried out in accordance with known procedures. Acid addition salts may be produced from the free bases in known manner, and vice-versa. Compound of formula (I) can also be prepared by further conventional processes, for example as described in the Examples, which processes are further aspects of the invention.

The starting materials used are known or may be prepared according to conventional procedures starting from known compounds, for example as described in the Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The compound of the invention and intermediates can also be converted into each other according to methods generally known to those skilled in the art.

In a further aspect, the invention relates to a compound of formula (IIa) in free form or in pharmaceutically acceptable salt form

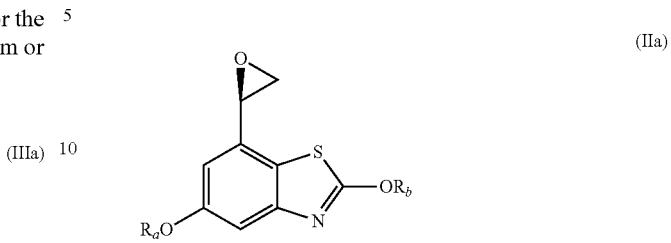

(IIa)

wherein $R_a$ and $R_b$ are protecting groups.

$R_a$ and $R_b$ may be independently selected from the group including tert-butyl, isopropyl and tert-butyldimethylsilyl.

In a further aspect, the invention relates to a compound of formula (IIIa-2) in free form or in pharmaceutically acceptable salt form

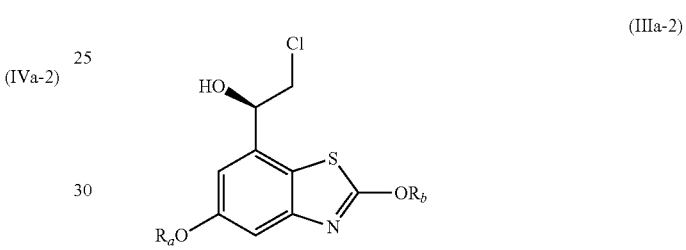

(IIIa-2)

wherein $R_a$ and $R_b$ are protecting groups.

$R_a$ and $R_b$ may be independently selected from the group including tert-butyl, isopropyl and tert-butyldimethylsilyl.

In a further aspect, the invention relates to a compound of formula (Ia) in free form or in pharmaceutically acceptable salt form

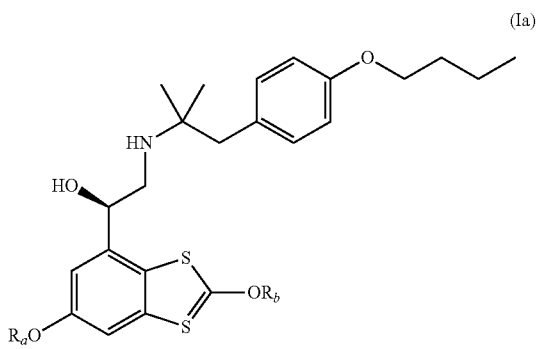

(Ia)

wherein $R_a$ and $R_b$ are protecting groups.

$R_a$ and $R_b$ may be independently selected from the group including tert-butyl, isopropyl and tert-butyldimethylsilyl.

In another aspect, the present invention provides a pharmaceutical composition comprising the compound of the present invention in free form or in pharmaceutically acceptable salt form and a pharmaceutically acceptable carrier. In particular, the invention relates to a pharmaceutical composition comprising a therapeutically effective amount of a compound of formula (I) in free form and one or more pharmaceutically acceptable carriers. In one embodiment, the invention relates to a pharmaceutical composition comprising a therapeutically effective amount of a compound of formula (I) in pharmaceutically acceptable salt form and one or more pharmaceutically acceptable carriers. In another embodiment, the invention relates to a pharmaceutical composition comprising a therapeutically effective amount of a compound of formula (I) in acetate salt form and one or more pharmaceutically acceptable carriers. In yet another embodiment, the invention relates to a pharmaceutical composition comprising a therapeutically effective amount of a compound of formula (I) in glycolate salt form and one or more pharmaceutically acceptable carriers.

The pharmaceutical composition can be formulated for particular routes of administration such as oral administration, transdermal application, parenteral administration, rectal administration, subcutaneous administration etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets.

These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The compound of the invention may be administered orally to preclinical species as a liquid dosage form with the drug in a solution or in a suspension vehicle. Solution vehicles can be composed of surfactant (e.g., cremophor or solutol), solvent (e.g., propylene glycol) and buffer agent (e.g. citric buffer). Suspension formulations can contain surfactant (e.g. Tween 80), a polymer agent (e.g., methyl cellulose (MC)) and a buffer agent (e.g., phosphate).

Examples of solution formulations suitable for preclinical studies are set out below:

| Ingredient (% w/w) | Solution 1 | Solution 2 |
|---|---|---|
| Cremophor RH40 | 10 | — |
| Solutol HS15 | — | 10 |
| Citric buffer 50 mM, pH 3 | 90 | 90 |

Preparation: free base or acetate salt (R)-7-(2-(1-(4-butoxyphenyl)-2-methylpropan-2-ylamino)-1-hydroxyethyl)-5-hydroxybenzo[d]thiazol-2(3H)-one) is first dissolved in the surfactant and mixed until a solution is obtained. Next the buffer is added and the solution mixed to provide a clear solution. Solution formulations 1 and 2 are able to support up to a 10 mg/mL dose. Both formulations are chemically and physically stable after 1 week at RT.

Examples of suspension formulations suitable for preclinical studies are set out below:

| Ingredient (% w/w) | Suspension 1 | Suspension 2 |
|---|---|---|
| 0.5% MC in 50 mM pH 6.8 phosphate buffer | 100 | 99.5 |
| Tween 80 | — | 0.5 |

Preparation: (R)-7-(2-(1-(4-butoxyphenyl)-2-methylpropan-2-ylamino)-1-hydroxyethyl)-5-hydroxybenzo[d]thiazol-2(3H)-one) is dispersed in the surfactant and mixed to homogenize the suspension. The polymer solution is then added drop wise and mixed. A homogeneous suspension is obtained with small particles. The suspension is chemically and physically stable after 1 week at RT.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

Said compositions are prepared according to conventional mixing, granulating or coating methods, respectively, and contain about 0.1-75%, or contain about 1-50%, of the active ingredient.

Suitable compositions for subcutaneous application include, for example, the compound of the invention with 2.5% poloxamer 407 in 0.9% sodium chloride. Examples of suitable devices for injectable compositions include infusion pumps such as Insulet's OmniPod system.

The compound of the invention may also be administered by multidose subcutaneous injection using an auto injector or PEN-injector. Formulation compositions suitable for such subcutaneous injection are set out below.

| Component | Formulation 1 | Formulation 2 |
|---|---|---|
| Compound A | 1.00 mg | 1.00 mg |
| acetic acid | 0.60 mg | 0.60 mg |
| mannitol | 50 mg | 50 mg |
| benzyl alcohol | 8.00 mg | 10.00 mg |
| sodium hydroxide 1N | adjusted to pH 5.0 | adjusted to pH 5.0 |
| water for injection | add up to 1.016 g | add up to 1.016 g |

Benzyl alcohol (in comparison to phenol or m-cresol) was found to be a particularly suitable preservative for a subcutaneous injection formulation.

Thus in one embodiment of the invention, there is provided a pharmaceutical composition comprising a therapeutically effective amount of Compound A, or a pharmaceutically acceptable salt thereof (for example Compound A in acetate salt form), and benzyl alcohol.

In a further embodiment of the invention, there is provided a pharmaceutical composition comprising a therapeutically effective amount of Compound A, or a pharmaceutically acceptable salt thereof (for example Compound A in acetate salt form), and between 0.1 and 10; 0.1 and 5; 0.5 and 2; 0.5 and 1.5; or 0.9 and 1.1% (w/v) benzyl alcohol.

Suitable compositions for transdermal application include an effective amount of a compound of the invention with a suitable carrier. Carriers suitable for transdermal delivery include absorbable pharmacologically acceptable solvents to assist passage through the skin of the host. A combination of PG/OA (propylene glycol/oleyl alcohol) is an example of suitable solvent. For example, transdermal devices may be in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compound of the present invention as active ingredient, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of formula (I) in free form or in pharmaceutically acceptable salt form, exhibits valuable pharmacological properties, e.g. beta-2-adrenoceptor modulating properties, e.g. as indicated in in vitro and in vivo tests as provided in the next sections and is therefore indicated for therapy or for use as research chemicals, e.g. as a tool compound.

The compound of the invention may be useful in the treatment of an indication selected from: muscular dystrophy, disuse-related atrophy, cachexia or sarcopenia.

Thus, as a further embodiment, the present invention provides the compound of formula (I) as defined herein, as a medicament. In an embodiment, the present invention relates to the compound of formula (I) for use as a medicament. In a further embodiment, the present invention relates to the compound of formula (I) for use in the treatment or prevention of muscular dystrophy, disuse-related atrophy, cachexia or sarcopenia.

Thus, as a further embodiment, the present invention provides the use of a compound of formula (I) in therapy. In a further embodiment, the therapy is selected from a disease which may be treated by activation of beta-2-adrenoceptor. In another embodiment, the disease is selected from muscular dystrophy, disuse-related atrophy, cachexia or sarcopenia.

In another embodiment, the invention provides a method of treating a disease which is treated by activation of beta-2-adrenoceptor comprising administration of a therapeutically acceptable amount of a compound of formula (I). In a further embodiment, the disease is selected from muscular dystrophy, disuse-related atrophy, cachexia or sarcopenia.

A further aspect of the invention thus relates to a method of treatment or prevention of muscular dystrophy, disuse-related atrophy, cachexia or sarcopenia comprising administering a therapeutically effective amount of a compound of formula (I) in free form or in pharmaceutically acceptable salt form to a subject in need thereof.

As a further embodiment, the present invention provides the use of a compound of formula (I) for the manufacture of a medicament. In a further embodiment, the medicament is for the treatment of a disease or disorder which may be treated by activation of beta-2 adrenoceptor. In another embodiment, the disease is selected from the afore-mentioned list, suitably muscle wasting diseases, more suitably muscular dystrophy, disuse-related atrophy, cachexia or sarcopenia.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition modulated by beta-2 adrenoceptor agonism. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

A further aspect of the invention thus relates to a combination comprising a therapeutically effective amount of a compound of formula (I) and one or more therapeutically active co-agents.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition modulated by beta-2 adrenoceptor agonism, wherein the medicament is prepared for administration with another therapeutic agent. The invention also provides the use of another therapeutic agent for treating a disease or condition modulated by beta-2 adrenoceptor agonism, wherein the medicament is administered with a compound of formula (I).

The invention also provides a compound of formula (I) for use in a method of treating a disease or condition modulated by beta-2 adrenoceptor agonism, wherein the compound of formula (I) is prepared for administration with another therapeutic agent. The invention also provides another therapeutic agent for use in a method of treating a disease or condition modulated by beta-2 adrenoceptor agonism, wherein the other therapeutic agent is prepared for administration with a compound of formula (I). The invention also provides a compound of formula (I) for use in a method of treating a disease or condition modulated by beta-2 adrenoceptor agonism, wherein the compound of formula (I) is administered with another therapeutic agent. The invention also provides another therapeutic agent for use in a method of treating a disease or condition modulated by beta-2 adrenoceptor agonism, wherein the other therapeutic agent is administered with a compound of formula (I).

The invention also provides the use of a compound of formula (I) for treating a disease or condition modulated by beta-2 adrenoceptor, wherein the patient has previously (e.g. within 24 hours) been treated with another therapeutic agent. The invention also provides the use of another therapeutic agent for treating a disease or condition modulated by beta-2 adrenoceptor, wherein the patient has previously (e.g. within 24 hours) been treated with a compound of formula (I).

In one embodiment, the other therapeutic agent is selected from testosterone, androgen agonists, or SARM (selective androgen receptor modulators); IGF-1 mimetics; myostatin and its receptor ActRIIA/B blockers; TGFbeta and activin blockers (as anti-atrophy agents);

Muf1/MAFbx E3 ligase inhibitors; HDAC inhibitors or any oncolytic agents (e.g. for cancer cachexia); anti-inflammatory agents like NSAIDs, TNF or IL-1b blockers; metabolic modulators like PPAR agonists or IL-15 mimetics; cardiovascular agents like b(1) blockers (e.g. nebivolol) or ARB (e.g. for cardiac cachexia); antisense oligos for exon-skipping (e.g. for dystrophy); an appetite enhancer such as ghrelin, progestin or MC-4 antagonists; high protein nutrient supplements and the like.

The pharmaceutical composition or combination of the present invention can be in unit dosage of about 0.05-1000 mg of active ingredient(s) for a subject of about 50-70 kg, or about 0.05-500 mg or about 0.05-250 mg or about 0.05-150 mg or about 0.05-100 mg, or about 0.05-50 mg or about 0.05-10 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compound of the present invention can be applied in vitro in the form of solutions, e.g., aqueous solutions, and in vivo either enterally, parenterally, advantageously subcutaneously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.01-500 mg/kg, or between about 0.01-100 mg/kg, or between about 0.01-1 mg/kg, or between about 0.01-0.1 mg/kg.

The activity of the compound of the present invention can be assessed by the following in vitro method. Further in vivo methods are described further in the Examples.

Test 1: In Vitro Cellular Functional Assay Using CHO Cells and Skeletal Muscle Cells cAMP: Human skeletal muscle cells (skMC) were obtained from Cambrex (catalog no CC-2561) and cultured in Skeletal Basal Medium (SKBM) obtained from Cambrex (catalog no #CC-3161). The cAMP responses were measured using cAMP dynamic 2 bulk HTRF-Assay kit obtained from Cisbio or Cis Competitive Intelligence (catalog no 62AM4PEC). skMC cells were cultured for 1 day in SKBM cell culture medium supplemented with 20% FCS in 384-well plates at 37° C., 5% $CO_2$. The next day, the cells were washed twice with 50 µL PBS, and differentiated for 3 days in serum-free SKBM in presence of 1 µM SB431542, a ALK 4/5 Inhibitor obtained from Sigma (catalog no S4317) at 37° C., 7.5% $CO_2$. On day 4, serum-free SKBM supplemented with 1 µM SB431542 was removed, cells were washed twice with 50 µL PBS and further differentiated for 1 day in serum-free SKBM without SB431542 (50 µL per well) at 37° C., 7.5% $CO_2$. Rat skMC and cardiomyocytes cells were isolated from neonatal rats in a standard way and treated as described above. Chinese hamster ovary (CHO) cells stably transfected with human β adrenoceptors (β1 or β2) were produced at Novartis Institutes for BioMedical Research and cultured as described before (J Pharmacol Exp Ther. 2006 May; 317(2):762-70).

Compounds were made up in stimulation buffer at 2× required concentration and 1:10 serial dilutions in stimulation buffer were prepared in 96-well plate (U-form). DMSO control was normalized to the DMSO content of the highest dilution, e.g. 0.1% DMSO (×2) for $10^{-5}$ M (×2) concentration of the first compound dilution. The assay was carried out in 384-well plates, in a 20 µL stimulation volume, and a final assay volume of 40 µL per well. On the day of experiment, culture medium was removed from 384-well cell culture plates by inverting and flicking the plate on stack of paper 2-3 times. 10 µL of fresh culture medium per well was first added in the 384-well plate. After 10 minutes of incubation at room temperature, 10 µL per well of working compounds dilutions were added to the cells and incubated for 30 minutes at room temperature in the dark. During this time, working solutions of reagents were prepared by diluting stock solutions of anti cAMP cryptate and cAMP D2 1:20 in lysis buffer, supplied with the kit. After 30 minutes of compound incubation, 10 µL of cAMP-D2 and 10 µL of anti cAMP cryptate were sequentially added to the assay plates. After 1 hour of incubation time at room temperature in the dark, the measurement was performed with the PheraStar (Excitation wavelength: 337 nm, Emission wavelengths: 620 and 665 nm).

$Ca^{2+}$: The human adrenergic Alpha1A CHO-K1 cell line was purchased from Perkin Elmer (ValiScreen™ Stable recombinant GPCR Cell line, catalog no ES-036-C, Lot no M1W-C1, Boston, Mass., USA). One day before the experiment, Alpha1A frozen cells (10 millions per ml and per vial) were thawed in a water bath at 37° C. The cell suspension was centrifuged for 5 minutes at 1,000 rpm and the cell pellet was resuspended in cell culture medium. Cells were seeded into black 384-well plates with clear bottom at a density of 8,000 cells per well in 50 µL of cell culture medium. Plates were incubated for about 24 hours at 37° C., 5% $CO_2$. The day of the experiment, the medium was removed using a cell washer (TECAN PW3). After the final wash there was 10 µL left in the wells. 40 µL of loading buffer were added and cells were loaded for 60 min at 37° C., 5% $CO_2$. Plates were washed with TECAN PW3 with 20 µL assay buffer left and were incubated for at least 20 minutes at RT before performing the FLIPR experiment. Compounds were then characterized in the agonist and/or antagonist mode. For assay validation, the same protocol was used with the fresh cells. In this case, cells were detached from a 150 $cm^2$ flask using 3 ml of Trypsin-EDTA, centrifuged and resuspended in cell culture medium.

Cells were stimulated by adding 5 µL of compounds (5×), using the FLIPR head. Compounds acting as agonists induce a transient increase of intracellular calcium. This was recorded on the FLIPR system. A measurement of the signal baseline was first recorded every second for 2 minutes before the injection of the compounds. Calcium measurements were performed by exciting the cells with the argon ion laser at 488 nm at 0.6 W laser power and recording the fluorescence signal with a CCD camera (opening of 0.4 sec) for 2 minutes. Low controls (unstimulated cells) were determined with the addition of 5 µL of assay buffer. High controls were determined with the addition of 5 µL of a known agonist at high concentration $EC_{100}$ (A-61603 at 1 µM) and a reference agonist compound was also added in each plate.

The compound of the invention exhibits efficacy in test assay 1 with an $EC_{50}$ of less than 10 nM. Specific activity is shown in example 10

Further specific activities of the compound of the invention are described in examples 11 to 15.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, $R_a$ NMR. Abbreviations used are those conventional in the art.

All starting materials, building blocks, reagents, acids, bases, dehydrating agents, solvents, and catalysts utilized to synthesise the compound of the present invention are either commercially available or can be produced by organic synthesis methods known to one of ordinary skill in the art (Houben-Weyl 4th Ed. 1952, Methods of Organic Synthesis, Thieme, Volume 21). Further, the compound of the present invention can be produced by organic synthesis methods known to one of ordinary skill in the art as shown in the following examples.

EXAMPLES

List of Abbreviations:
1M one molar
APCI atmospheric-pressure chemical ionization
aq aqueous
AR adrenoceptor
atm atmosphere
br broad
cm centimeters
d doublet
dd double doublet
ddd double double doublet
$(DHDQ)_2PHAL$ Hydroquinidine 1,4-phthalazinediyldiether
DMAC dimethylacetamide
DMSO dimethylsulfoxide
DSC differential scanning calorimetry
ee enantiomeric excess
equiv equivalent
ES electron-spray
g grams
h hours
HPLC high performance liquid chromatography
HRMS high resolution mass spectroscopy
m multiplet
MC methyl cellulose mbar millibar
MeOH methanol
min minutes
ml milliliters
MS mass spectroscopy
MTBE methyl tert-butyl ether
nm nanometers
NMR nuclear magnetic resonance
RT retention time
r.t. room temperature
s singlet
sat. saturated
sept septet
t triplet
TFA trifluoroacetic acid
μm micrometers
w/v weigh/volume
XRPD x-ray powder diffraction Unless otherwise indicated, HPLC/MS spectra were recorded on an Agilent 1100 series LC/Agilent MS 6210 Quadrupole. A Waters Symmetry C8 column (3.5 um; 2.1×50 mm) (WAT200624) was used. The following gradient method was applied (%=percent by volume): A=water+0.1% TFA/B=acetonitrile+0.1% TFA; 0.0-2.0 min 90A:10B-5A:95B; 2.0-3.0 min 5A:95B; 3.0-3.3 min 5A:95B-90A:10B; flow 1.0 ml/min; column temperature 50° C. All compounds were ionized in APCI mode.

$^1$H-NMR spectra were recorded on a Varian Mercury (400 MHz) or Bruker Advance (600 MHz) machine.

Optical rotation was measured on a Perkin Elmer Polarimeter 341.

LCMS Condition for Example 2b, 2c, 2d, 2e, 2q:

Mass spectra station: Agilent 6130 quadrupole LC/MS with Agilent 1200 HPLC; Column: Agilent Zorbax SB-C18 (Rapid resolution), 2.1*30 mm, 3.5 μm; Mobile phases: B: 0.1% formic acid in water; C: 0.1% formic acid in MeCN; 1.0 min to 6.0 min, 95% B to 5% B, and 5% C to 95% C; 6.0 min to 9.0 min, 5% B and 95% C; post time: 2.0 min; flow rate: 0.8 ml/min; column temperature: 30° C.; UV detection: 210 nm and 254 nm; MS scan positive and negative: 80-1000; Ionization method: API-ES.

HRMS Conditions for Example 2f:

Instrument: Waters Acquity UPLC coupled with Synapt Q-TOF MS; Column: Waters Acquity UPLC BEH C18, 2.1*50 mm, 1.7 μm Mobile Phase: A: 0.1% formic acid in water, B: 0.1% formic acid in Acetonitrile; Column temperature: at room temperature; UV detection: scan from 190 nm to 400 nm; Flow rate: 0.5 mL/min;

Gradient Condition:

| Time [min.] | Phase B [%] | |
|---|---|---|
| 0 | 5 | |
| 1 | 5 | Start of acquisition |
| 9 | 95 | |
| 11 | 95 | End of acquisition |
| 11.10 | 5 | |
| 14 | 5 | Next injection |

Ionization method: ESI+; MS scan range: 100-1000 m/z.

Intermediate A:
2-(4-butoxyphenyl)-1,1-dimethyl-ethylamine a) 4-(2-methyl-2-nitropropyl)phenol A mixture of 4-(hydroxymethyl)phenol (20 g), KOtBu (27.1 g) and DMAC (200 mL) was stirred with magnetic stirrer. 2-nitropropane (21.5 g) was added slowly within 20 min. The mixture was heated to 140° C. for 5 hr before cooled to r.t. The mixture was added slowly to cool HCl aqueous solution (3.0%, 600 mL), then extracted with MTBE (300 ml*1, 200 ml*1). The organic layers were combined, washed with water (300 ml*2) and sat. NaCl aqueous solution (50 ml*1), then dried with anhydrous Na$_2$SO$_4$. The mixture was filtered and concentrated under vacuum to give light-yellow solid (28.5 g), which was used for next step without further purification.

[M−1]$^+$=194.2; RT=5.3 minutes $^1$H-NMR (400 MHz, CDCl$_3$) ppm 6.96 (d, J=8.5 Hz, 2H), 6.75 (d, J=8.5 Hz, 2H), 3.11 (s, 2H), 1.56 (s, 6H).

b) 1-butoxy-4-(2-methyl-2-nitropropyl)benzene

The mixture of 4-(2-methyl-2-nitropropyl)phenol (20.4 g), 1-bromobutane (28.7 g), DMAC (200 ml), K$_2$CO$_3$ (21.6 g), tetrabutylammonium iodide (38.7 g) was stirred with magnetic stirrer and heated to 85° C. for 17 h. The mixture was cooled to 0-10° C. and water (700 ml) was added. The mixture was extracted with MTBE (300 ml*1, 200 ml*1). The combined organic phases were washed with water (250 ml*2), then concentrated under vacuum to give a red-brown oil (27.8 g), which was used in the next step without further purification.

$^1$H-NMR (400 MHz, CDCl$_3$) ppm 7.0 (d, J=8.8 Hz, 2H), 6.81 (d, J=8.8 Hz, 2H), 3.93 (t, J=6.6 Hz, 2H), 3.12 (s, 2H), 1.74 (m, 2H), 1.56 (s, 6H), 1.48 (m, 2H), 0.97 (t, 3H).

c) 2-(4-butoxyphenyl)-1,1-dimethyl-ethylamine

In a hydrogenating reactor (1 L), a solution of 1-butoxy-4-(2-methyl-2-nitropropyl)benzene (27.8 g) in AcOH (270 ml) was added followed by wet Raney Ni (7.0 g). The mixture was purged with H$_2$ for 3 times, then heated to 60° C. and kept stirring under 5.0 atm for 16 h. The mixture was filtered, the total filtrate was concentrated under vacuum. The resulting residue was diluted with water (150 ml)/n-heptane (80 ml), the aqueous layer was washed with n-heptane (80 ml) again. The aqueous layer was adjusted with NaOH (~20%) to pH ~11, then extracted with MTBE (100 ml*1) and EtOAc (150 ml*2). The medium layer was discarded. All top layers were combined and washed with saturated NaHCO$_3$ (100 ml) and saturated NaCl (100 ml) before being dried with anhydrous Na$_2$SO$_4$. After filtration, the mixture was concentrated. The resulting residual was stirred and HCl solution in isopropyl alcohol (2M, 40 ml) was added. The slurry was heated to 60° C. and n-heptane (120 ml) was added. The mixture was cooled to 20° C., then filtered, the cake was washed with some n-heptane. The white solid was dried in air for 2 days to give 10 g of pure HCl salt of product. Yield: 35.2%.

[MH]+=222.2; RT=5.0 minutes $^1$H-NMR (400 MHz, d-DMSO) ppm 8.13 (s, 3H), 7.12 (d, J=8.6 Hz, 2H), 6.88 (d, J=8.5 Hz, 2H), 3.93 (t, J=6.4 Hz, 2H), 2.80 (s, 2H), 1.67 (m, 2H), 1.42 (m, 2H), 1.18 (s, 6H), 0.92 (t, 3H).

Example 1

(R)-7-(2-(1-(4-butoxyphenyl)-2-methylpropan-2-ylamino)-1-hydroxyethyl)-5-hydroxybenzo[d]thiazol-2(3H)-one

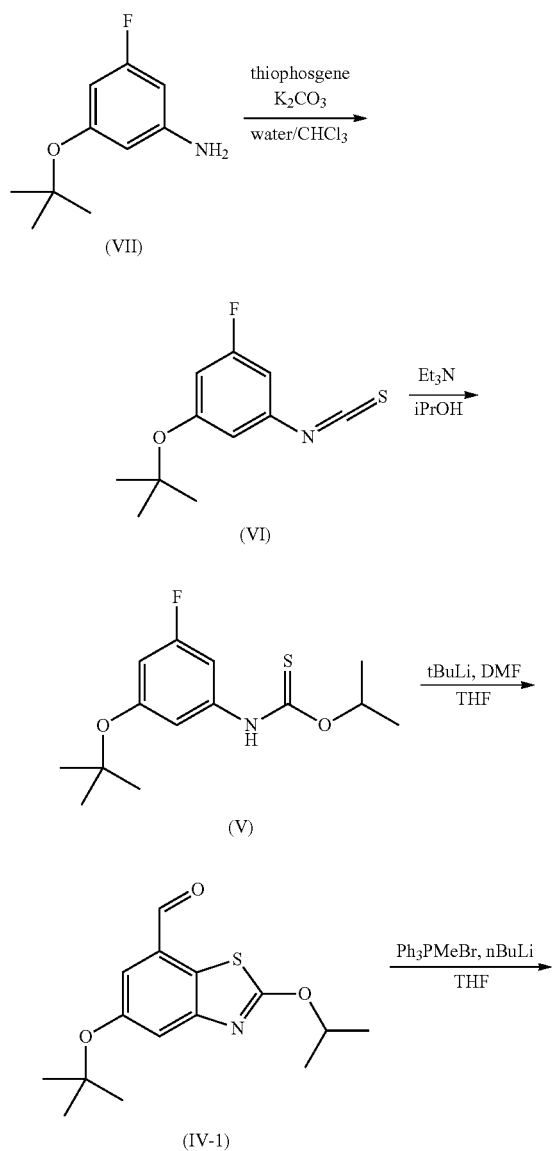

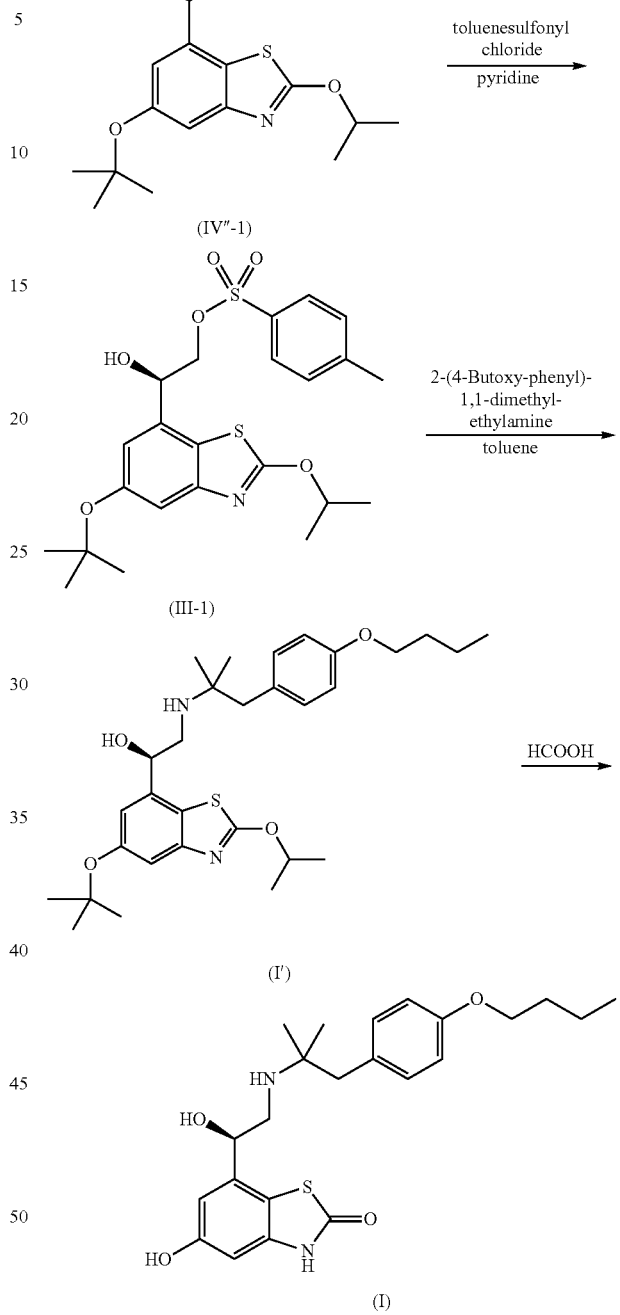

a) 1-tert-Butoxy-3-fluoro-5-isothiocyanatobenzene

Thiophosgene (33.6 g) in CHCl$_3$ (250 ml) and K$_2$CO$_3$ (64.7 g) in H$_2$O (450 ml) are added, separately and simultaneously, drop wise to a solution of 3-tert-Butoxy-5-fluorophenyl-amine (42.9 g) in CHCl$_3$ (350 ml) at 0° C. The reaction mixture is warmed to room temperature over night. The organics are separated and washed with water (3×), brine (1×), dried over MgSO$_4$, filtered and the solvent removed in vacuo. The title compound is obtained by flash column chromatography (silica, eluent dichloromethane/iso-hexane 1:3).

$^1$H NMR (CDCl$_3$, 400 MHz); 6.70 (m, 3H), 1.40 (s, 9H).

b) (3-tert-Butoxy-5-fluoro-phenyl)-thiocarbamic acid 0-isopropyl ester 1-tert-Butoxy-3-fluoro-5-isothiocyanatobenzene (24.0 g) and triethylamine (10.9 g) are dissolved in iso-propanol (150 ml). The reaction mixture is refluxed for 18 hours and the solvent is removed by vacuo. The crude product is dissolved in hexane: diethyl ether (19:1). The diethyl ether is removed in vacuo and the solution is cooled to 0° C. for 3 hours. The solution is filtered to give the title compound.

$^1$H NMR (CDCl$_3$, 400 MHz); 8.10 (br s, 1H), 6.65 (br s, 2H), 6.45 (ddd, 1H) 5.60 (sept, 1H), 1.35 (d, 6H), 1.30 (s, 9H).

c) 5-tert-Butoxy-2-isopropoxy-benzothiazole-7-carbaldehyde (3-tert-Butoxy-5-fluoro-phenyl)-thiocarbamic acid 0-isopropyl ester (2.2 g) is dissolved in dry tetrahydrofuran (20 ml) The reaction mixture is cooled to −78° C. and tert-butyl lithium (15.2 ml, of 1.5 M solution) is added over 20 minutes. The reaction mixture is then warmed to −10° C. for 75 minutes. The reaction mixture is then re-cooled to −78° C., N,N-dimethyl-formamide (1.5 g) is added and the reaction mixture is slowly warmed to room temperature then stirred at −10° C. for 1 hour. The reaction mixture is quenched with HCl$_{(aq)}$ (5 ml, of a 2 M solution), the organics are separated between ethyl acetate/water and removed in vacuo. The title compound is obtained by flash column chromatography (silica, eluent ethyl acetate/iso-hexane 1:9).

MS (ES+) m/e 294 (MH$^+$).

d) 5-tert-Butoxy-2-isopropoxy-7-vinylbenzothiazole

Ph$_3$PMe.Br (5.0 g) is dissolved in dry tetrahydrofuran (100 ml) under argon. N-butyl lithium (8.8 ml, of 1.6 M solution) is added at room temperature over 10 minutes and reaction mixture stirred for a further 30 minutes. A solution of 5-tert-Butoxy-2-isopropoxy-benzothiazole-7-carbaldehyde (1.25 g) in dichloromethane (40 ml) is added drop wise to the reaction mixture and the reaction mixture is stirred for 4.5 hours at room temperature. The solvent is removed in vacuo, redissolved in ethyl acetate, washed with water (3×), brine (1×), dried over MgSO$_4$, filtered and the solvent removed in vacuo. The title compound is obtained by flash column chromatography (silica, eluent ethyl acetate/iso-hexane 1:9).

MS (ES+) m/e 292 (MH$^+$).

e) (R)-1-(5-tert-Butoxy-2-isopropoxy-benzothiazol-7-yl)-ethane-1,2-diol

K$_3$Fe(CN)$_6$ (1.2 g), K$_2$CO$_3$ (0.5 g), (DHQD)$_2$PHAl (19 mg) are dissolved in tert-butanol/water (15 ml, 1:1 mix) under argon and stirred for 15 minutes. The reaction mixture is cooled to 0° C. and OsO$_4$ (3.1 mg) is added followed by 5-tert-Butoxy-2-isopropoxy-7-vinylbenzothiazole (0.35 g). The reaction mixture is stirred over night at room temperature. The reaction mixture is quenched with sodium-meta-bisulphate (1 g) and stirred for 1.5 hours. Ethyl acetate is added, the organics are separated, washed with (2×) water, (1×) brine, dried over MgSO$_4$, filtered and the solvent removed in vacuo. The title compound is obtained by flash column chromatography (silica, eluent ethyl acetate/iso-hexane 2:5).

MS (ES+) m/e 326 (MH$^+$).

f) (R)-2-(5-tert-butoxy-2-isopropoxybenzo[d]thiazol-7-yl)-2-hydroxyethyl-4-methylbenzenesulfonate Into a 500-ml 3-necked round-bottom flask, purged and maintained with an inert atmosphere of nitrogen, was placed a solution of (R)-1-(5-tert-butoxy-2-isopropoxy-benzo[d]thiazol-7-yl)ethane-1,2-diol (20 g, 59.05 mmol) in pyridine (240 ml) and 4A molecular sieves (5 g). This was followed by the addition of a solution of toluenesulfonic acid chloride (tosyl chloride) (15.3 g, 79.73 mmol) in pyridine (60 ml) dropwise with stirring at 0° C. The resulting solution was stirred for 4 h at room temperature. The reaction was then quenched by the addition of 1000 ml of 1M hydrogen chloride. The resulting solution was extracted with 2×300 ml of ethyl acetate and the organic layers are combined. The organic phase was washed with 1×500 ml of 1M hydrogen chloride, 1×500 ml of 10% sodium bicarbonate and 300 ml of brine. The mixture was dried over anhydrous sodium sulfate and concentrated under vacuum. The residue was applied onto a silica gel column with ethyl acetate/petroleum ether (1:10). This resulted in 26 g (87%) of (R)-2-(5-tert-butoxy-2-isopropoxybenzo[d]thiazol-7-yl)-2-hydroxyethyl 4-methylbenzenesulfonate as yellow oil.

LC/MS R$_T$=2.47 min; (m/z): 480 [M+H]$^+$ $^1$H-NMR: (400 MHz, DMSO-d$_6$): δ (ppm) 7.57 (d, 2H); 7.36 (d, 2H); 7.17 (d, 1H); 6.79 (d, 1H); 6.32 (d, 1H); 5.37-5.26 (m, 1H); 4.97-4.90 (m, 1H); 4.12-4.00 (m, 2H); 2.40 (s, 3H); 1.45-1.38 (m, 6H); 1.32 (s, 9H).

q) (R)-1-(5-tert-butoxy-2-isopropoxybenzo[d]thiazol-7-yl)-2-(1-(4-butoxyphenyl)-2-methylpropan-2-ylamino)ethanol Into a 1000-mLml 4-necked round-bottom flask was placed a solution of (R)-2-(5-tert-butoxy-2-isopropoxy-benzo[d]thiazol-7-yl)-2-hydroxyethyl-4-methylbenzenesulfonate (26 g, 51.55 mmol, 1.00 equiv) in toluene (320 mLml) and 2-(4-butoxyphenyl)-1,1-dimethyl-ethylamine (intermediate A) (22 g, 99.47 mmol, 1.93 equiv). The solution was stirred for 24 h at 90° C. in an oil bath. The resulting mixture was concentrated under vacuum. The residue is applied onto a silica gel column with ethyl acetate/petroleum ether (1:8). This resulted in 16 g (58%) of (R)-1-(5-tert-butoxy-2-isopropoxybenzo[d]thiazol-7-yl)-2-(1-(4-butoxyphenyl)-2-methylpropan-2-ylamino)ethanol as light yellow oil.

LC/MS: R$_T$=2.24 min (m/z): 529 [M+H]$^+$ $^1$H-NMR: (600 MHz, DMSO-d$_6$): δ (ppm) 7.12 (s, 1H); 6.83 (d, 2H); 6.77 (s, 1H); 6.63 (d, 2H); 5.80 (br. s, 1H); 5.38-5.30 (m, 1H); 4.70-4.66 (m, 1H); 3.90 (t, 2H); 2.81-2.61 (m, 2H); 2.50-2.39 (m, 2H); 1.71-1.62 (m, 2H); 1.47-1.41 (m, 2H); 1.41 (d, 6H); 1.22 (s, 9H); 0.91 (q, 3H); 0.88 (s, 3H); 0.83 (s, 3H).

h) (R)-7-(2-(1-(4-butoxyphenyl)-2-methylpropan-2-ylamino)-1-hydroxyethyl)-5-hydroxybenzo[d]thiazol-2(3H)-one A solution of (R)-1-(5-tert-butoxy-2-isopropoxybenzo[d]thiazol-7-yl)-2-(1-(4-butoxyphenyl)-2-methylpropan-2-ylamino)ethanol (3.5 g) in formic acid (40 ml) was stirred for 68 h at ambient temperature. 50 ml of water was added, and the resulting mixture was evaporated to dryness (rotary evaporator, 15 mbar, 40° C.) to give 3.8 g of crude product. This material was partitioned between saturated aqueous sodium bicarbonate (50 ml) and ethyl acetate (50 ml) in order to remove formic acid. The aqueous layer was extracted 3× with ethyl acetate (30 ml each). The combined organic extracts were dried over magnesium sulfate, filtered and concentrated to give 3 g of crude free-base. This material was flash-chromatographed (silica gel; gradient 0-60% methanol in dichloromethane). Pure fractions were collected and evaporated to dryness to give 1.74 g of an amorphous semi-solid.

This material was subjected to chiral preparative chromatography [column: Chiralpak IC (20 um) 7.65×37.5 cm; eluent: n-heptane/dichloromethane/ethanol/diethylamine 50:30:20 (+0.05 diethylamine); flow rate=70 ml/min; concentration: 2.5 g/50 ml eluent; detection: UV, 220 nm] to give pure enantiomer (100% ee).

This material was dissolved in 45 ml of acetonitrile at 60° C. The solution was allowed to cool to ambient temperature over 18 h, upon which precipitation occurred. The mixture was diluted with 5 ml of cold (4° C.) acetonitrile and filtered through a Buchner funnel. The filter cake was washed twice with cold acetonitrile. Then the wet solid was collected and dried in vacuo (0.2 mbar) at ambient temperature overnight to give 1.42 g of (R)-7-(2-(1-(4-butoxyphenyl)-2-methylpropan-2-ylamino)-1-hydroxyethyl)-5-hydroxybenzo[d]thiazol-2(3H)-one as a colorless powder.

LC/MS: $R_T$=1.81 min (m/z): 431 [M+H]$^+$ $^1$H-NMR: (600 MHz, DMSO-d$_6$): δ (ppm) 11.5 (br. s, 1H); 9.57 (br. s, 1H); 6.99 (d, 2H); 6.76 (d, 2H); 6.52 (s, 1H); 6.47 (s, 1H); 5.63 (br. s, 1H); 4.53-4.48 (m, 1H); 3.90 (t, 2H); 2.74-2.63 (m, 2H); 2.54-2.45 (m, 2H); 1.71-1.62 (m, 2H); 1.49-1.40 (m, 2H); 0.93 (q, 3H); 0.89 (s, 6H). Optical rotation: $[α]_D^{22}$=−43° (c=1.0 g/100 ml MeOH).

Example 2

Alternative route to (R)-7-(2-(1-(4-butoxyphenyl)-2-methylpropan-2-ylamino)-1-hydroxyethyl)-5-hydroxybenzo[d]thiazol-2(3H)-one

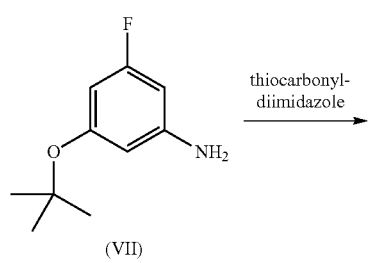

(VII)

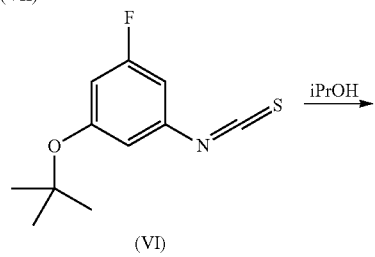

(VI)

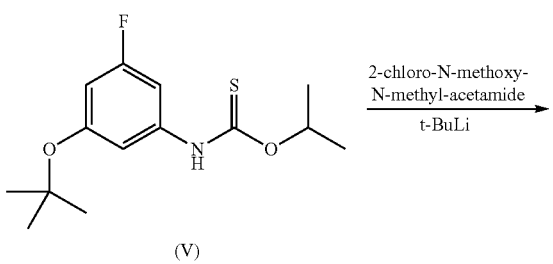

(V)

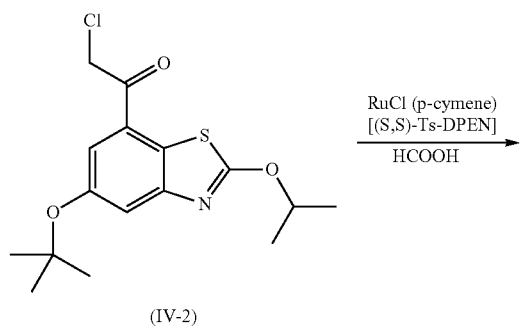

(IV-2)

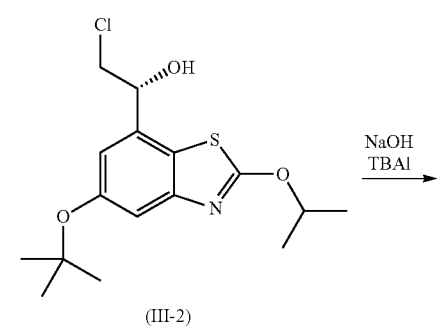

(III-2)

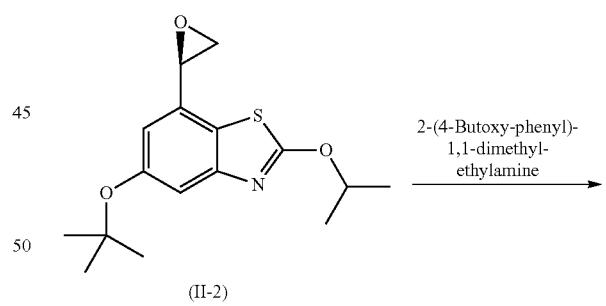

(II-2)

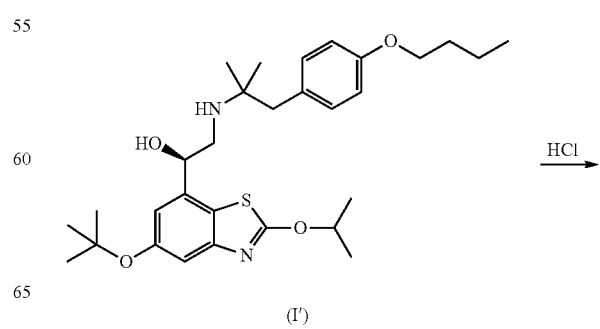

(I')

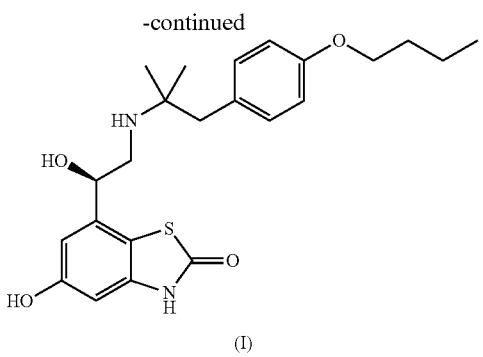

(I)

a) 1-tert-Butoxy-3-fluoro-5-isothiocyanato-benzene 1,1'-Thiocarbonyldiimidazole (423 g, 2.37 mol) was dissolved in dichloromethane (3200 ml). The mixture was stirred under $N_2$ atmosphere while a solution of 3-tert-butoxy-5-fluoroaniline (435 g, 2.37 mol) in dichloromethane (800 ml) was added slowly within 2 h. Then the mixture was kept stirring at 20° C. for 16 h. The mixture was diluted with water (3000 ml). The separated dichloromethane phase was washed again with water (3000 ml) before dried with anhydrous $Na_2SO_4$ for 2 h. The mixture was filtered and the filtrate was concentrated under vacuum to remove solvent to give 1-tert-butoxy-3-fluoro-5-isothiocyanato-benzene (499 g).

$^1$H-NMR (400 MHz, $CDCl_3$): 6.63-6.68 (m, 3H), 1.37 (s, 9H).

b) (3-tert-Butoxy-5-fluoro-phenyl)-thiocarbamic acid 0-isopropyl ester

To a solution of 1-tert-butoxy-3-fluoro-5-isothiocyanato-benzene (460 g, 2.04 mol) in anhydrous isopropyl alcohol (3250 ml) was added triethylamine (315 g, 3.06 mol). The mixture was heated to reflux under $N_2$ atmosphere for 16 h and the temperature was cooled to 40-50° C. After concentration, the resulting dark residue was diluted with n-heptane (1000 ml) and heated to 60° C. The mixture was slowly cooled to 25° C., at the same time seeding was added. A slurry was observed and stirred at 25° C. for 16 h before being cooled slowly to 0-10° C. within 2 h. After filtration and washing with n-heptane (200 ml), the collected solid was dried in oven under vacuum at 40-45° C. for 18 h to give (3-tert-Butoxy-5-fluoro-phenyl)-thiocarbamic acid 0-isopropyl ester (453.1 g).

LCMS: $[M+H]^+$=286.1; RT=7.2 minutes $^1$H-NMR (400 MHz, $CDCl_3$): 8.18 (s, 1H), 6.81 (m, 2H), 6.51 (dt, J=10.2 Hz, 1H), 5.66 (heptet, J=6.3 Hz, 1H), 1.42 (d, J=6.2 Hz, 6H), 1.37 (s, 9H).

c) 1-(5-tert-Butoxy-2-isopropoxy-benzothiazol-7-yl)-2-chloro-ethanone

Under a nitrogen atmosphere, a solution of tert-butyllithium (481 ml, 737.6 mmol, 1.6 M) was added dropwise to a solution of (3-tert-Butoxy-5-fluoro-phenyl)-thiocarbamic acid 0-isopropyl ester (200 g, 700.83 mmol) in 2-Me-THF (1600 ml) at temperature below −65° C. The reaction temperature was warmed to −35° C., and a second portion of tert-butyllithium (388 ml, 737.6 mmol, 1.9 M) was added slowly while keeping the temperature below −35° C. The reaction mixture was then stirred at this temperature for 3 h and cooled down to −70° C. A solution of N-methyl-N-methoxy chloroacetamide (96.4 g, 700.83 mmol) in 2-MeTHF (300 ml) was added to the reaction mixture while keeping the temperature below −70° C. The mixture was then warmed to −30° C. and stirred for 45 minutes. The cold reaction mixture was quenched by dropwise addition of 30% HCl in isopropanol (240 g) followed by the addition of 1500 ml water. The organic layer was washed sequentially with 1000 ml water, 1500 ml saturated aqueous $NaHCO_3$ and 1500 ml brine. After concentration, the resulting light brown residue was added to isopropanol (135 ml). The mixture was warmed to 50° C. and cooled down slowly to 25° C. n-heptane (135 ml) was added dropwise to the solution and the mixture was stirred overnight. The slurry was filtered and the filter cake was washed with n-heptane (40 ml) followed by another portion of n-heptane (20 ml). The cake was dried under vacuum to yield 1-(5-tert-butoxy-2-isopropoxy-benzothiazol-7-yl)-2-chloro-ethanone as off-white powder (42.8 g, 17.9% yield).

$^1$H NMR (400 MHz, $CDCl_3$): 7.60 (d, J=2.0 Hz, 1H), 7.45 (d, J=2.0 Hz, 1H), 5.40 (heptet, J=6.3 Hz, 1H), 4.77 (s, 2H), 1.47 (d, J=6.3 Hz, 6H), 1.40 (s, 9H).

LCMS: $[M+H]^+$=342.1, RT=7.29 min.

d) (R)-1-(5-tert-Butoxy-2-isopropoxy-benzothiazol-7-yl)-2-chloro-ethanol

A suspension of 1-(5-tert-butoxy-2-isopropoxybenzo[d]thiazol-7-yl)-2-chloro-ethanone (70 g, 204.8 mmol) and RuCl(p-cymene)[(S,S)-Ts-DPEN] (1.954 g, 3.07 mmol) in methanol/DMF (1330 ml/70 ml) was degassed and refilled with $N_2$ three times. A degassed preformed mixture of formic acid (28.3 g) in $Et_3N$ (124.3 g) was added slowly while keeping the internal temperature between 15 to 20° C. The resulting yellow suspension was warmed up to 30° C. After 2 h the reaction mixture is cooled to 25° C., water (750 ml) was then added into the reaction mixture followed by the addition of acetic acid (56 ml) in one portion. The mixture was concentrated and then diluted with TBME (1000 ml). Aqueous phase was separated and extracted with TBME (1000 ml). The combined organic phase was washed sequentially with water and brine and then dried with $Na_2SO_4$ and concentrated under vacuum to give (R)-1-(5-tert-Butoxy-2-isopropoxy-benzothiazol-7-yl)-2-chloro-ethanol (72 g).

LCMS (method A): $[M+H]^+$=343.1, RT=5.67 min.

$^1$H NMR (400 MHz, $CDCl_3$): 7.29 (d, J=2.0 Hz, 1H), 6.83 (d, J=2.0 Hz, 1H), 5.37 (heptet, J=6.3 Hz, 1H), 4.96 (m, 1H), 3.74 (m, 2H), 3.01 (s, 1H), 1.46 (d, J=6.2 Hz, 6H), 1.36 (s, 9H).

e) (R)-5-tert-Butoxy-2-isopropoxy-7-oxiranyl-benzothiazole

To a solution of (R)-1-(5-tert-butoxy-2-isopropoxybenzo[d]thiazol-7-yl)-2-chloro-ethanol (140 g, 407.1 mmol) in TBME (420 ml) was added dropwise NaOH aqueous solution (2M, 420 ml) followed by tetrabutylammonium iodide (7.52 g, 20.36 mmol) added in one portion. After 4 h at 26° C., 400 ml TBME was added and the organic layer was separated. The aqueous layer was extracted with TBME (400 ml). The combined organic layers were washed with water (400 ml) and brine (400 ml) to give (R)-5-tert-butoxy-2-isopropoxy-7-oxiranyl-benzothiazole (122 g).

LCMS: [M+H]⁺=308.0, RT=6.80 min.
¹H NMR (400 MHz, CDCl₃) ppm 7.28 (d, J=2.0 Hz, 1H), 6.85 (d, J=2.0 Hz, 1H), 5.38 (m, 1H), 3.96 (m, 1H), 3.15 (dd, J=4.3, 5.5 Hz, 1H), 2.94 (dd, J=4.3, 5.5 Hz, 1H), 1.45 (d, J=Hz, 6H), 1.37 (s, 9H).

f) (R)-1-(5-tert-butoxy-2-isopropoxybenzo[d]thiazol-7-yl)-2-(1-(4-butoxyphenyl)-2-methylpropan-2-ylamino)ethanol (R)-5-tert-butoxy-2-isopropoxy-7-oxiranyl-benzothiazole (145 g, 471.7 mmol) and 2-(4-butoxy-phenyl)-1,1-dimethyl-ethylamine (114.8 g, 518.9 mmol) were dissolved in DMSO (850 ml). The reaction mixture was heated to 80° C. and stirred for 27 h. The mixture was then cooled to 25° C. and added to a stirred mixture of water (1500 ml) and TBME (1500 ml). The aqueous layer was separated and extracted with TBME (1000 ml). The combined organic layers were sequentially washed with water (1500 ml) and brine (1000 ml), dried with anhydrous Na₂SO₄. After concentration, the residue was purified by column chromatography (eluting with 10% of EtOAc in n-heptane to 33% of EtOAc in n-heptane). Solid product (R)-1-(5-tert-butoxy-2-isopropoxybenzo[d]thiazol-7-yl)-2-(1-(4-butoxyphenyl)-2-methylpropan-2-ylamino)ethanol was obtained (140 g) as off-white solid.

HRMS: [M+1] 529.2996
¹H NMR (400 MHz, CDCl₃): 7.26 (m, 1H), 7.01 (m, 1H), 6.99 (m, 1H), 6.78-6.80 (m, 3H), 5.39 (m, 1H), 4.65 (dd, J=3.8, 8.8 Hz, 1H), 3.83 (t, J=6.4 Hz, 2H), 2.96 (dd, J=3.8, 12 Hz, 1H), 2.74 (dd, J=8.8, 12 Hz, 1H), 2.60 (dd, J=13.6, 17.6 Hz, 2H), 1.72-1.79 (m, 2H), 1.50 (m, 2H), 1.46 (d, J=2.0 Hz, 3H), 1.45 (d, J=2.0 Hz, 3H), 1.35 (s, 9H), 1.06 (s, 3H), 1.04 (s, 3H), 0.98 (t, J=7.2 Hz, 3H).

q) (R)-7-(2-(1-(4-butoxyphenyl)-2-methylpropan-2-ylamino)-1-hydroxyethyl)-5-hydroxybenzo[d]thiazol-2(3H)-one To (R)-1-(5-tert-butoxy-2-isopropoxybenzo[d]thiazol-7-yl)-2-(1-(4-butoxyphenyl)-2-methylpropan-2-ylamino)ethanol (7.5 g) in isopropanol (30 ml) and water (25 ml) was added 1M HCl aqueous solution (43 ml). The reaction mixture was then heated to 60° C. and stirred for 2.5 h. The mixture was cooled to 50° C., and then 2M NaOH aqueous solution (18 ml) was added slowly to adjust pH between 8.2-8.4. The reaction mixture was then cooled to 30° C., followed by extraction with TBME (first time with 40 ml, the second time with 25 ml). Two organic layers were combined and washed with water (38 ml for two times) before drying with anhydrous Na₂SO₄. After filtration, the filtrate was concentrated, and then dissolved in MeCN (145 ml). The solution was treated with active carbon (0.6 g) and heated to 60° C. After a second filtration, the cake was washed with MeCN (10 ml for two times), the filtrate was crystallized at 60° C. to gain (R)-7-(2-(1-(4-butoxyphenyl)-2-methylpropan-2-ylamino)-1-hydroxyethyl)-5-hydroxybenzo[d]thiazol-2(3H)-one (3.8 g). e.e. =97.6%.

LCMS (method A): [M+H]⁺=431.2
¹H NMR (400 MHz, DMSO-d₆): 9.5 (br. s, 1H), 6.81 (d, J=8.5 Hz, 2H), 6.57 (d, J=8.6 Hz, 2H), 6.33 (d, J=2.2 Hz, 1H), 6.30 (d, J=2.2 Hz, 1H), 4.43 (br. s, 1H), 3.69 (t, J=6.4 Hz, 2H), 2.58-2.59 (m, 2H), 2.24-2.31 (m, 2H), 1.41-1.48 (m, 2H), 1.15-1.25 (m, 2H), 0.78 (s, 6H), 0.70 (t, J=7.4 Hz, 3H).

Example 3

(R)-7-(2-(1-(4-butoxyphenyl)-2-methylpropan-2-ylamino)-1-hydroxyethyl)-5-hydroxybenzo[d]thiazol-2(3H)-one acetate salt 500 mg (1.161 mmol) of free base (R)-7-(2-(1-(4-butoxyphenyl)-2-methylpropan-2-ylamino)-1-hydroxyethyl)-5-hydroxybenzo[d]thiazol-2(3H)-one was suspended in 10.0 ml acetonitrile and 0.25 ml water in a 50 ml four-necked flask and paddle stirred at r.t. The suspension was heated at an internal temperature of 50° C. (jacket temperature 75° C.) and 72 mg acetic acid (1.161 mmol) was added (a clear yellow solution was formed). The solution was cooled down over 30 min. at r.t. and 0.15 ml water added.

The solution was then seeded with (R)-7-(2-(1-(4-butoxyphenyl)-2-methylpropan-2-ylamino)-1-hydroxyethyl)-5-hydroxybenzo[d]thiazol-2(3H)-one acetate and stirred overnight (16 h) at r.t. The suspension was then filtered at r.t. through a glass filer and washed three times with 1 ml acetonitrile. 510 mg of wet filter cake was dried in a drying oven overnight (16 h) at r.t. to dryness. Yield: 508 mg white powder (89.1%)

Preparation of (R)-7-(2-(1-(4-butoxyphenyl)-2-methylpropan-2-ylamino)-1-hydroxyethyl)-5-hydroxybenzo[d]thiazol-2(3H)-one acetate seeds 57.0 mg (0.132 mmol) of free base (R)-7-(2-(1-(4-butoxyphenyl)-2-methylpropan-2-ylamino)-1-hydroxyethyl)-5-hydroxybenzo[d]thiazol-2(3H)-one and 8.03 mg (0.132 mmol) acetic acid were dissolved in 1.0 ml acetonitrile and 0.05 ml water. The solution was stirred at r. t. with a magnetic stirrer stirred. Precipitation took place over night. The solution was then filtered at r.t. through a glass filter and washed three times with 0.5 ml acetonitrile. The wet filter cake was dried in a drying oven overnight (16 h) at r. t. to dryness. Yield: 57 mg white powder

Example 3a

Alternative procedure for the formation of (R)-7-(2-(1-(4-butoxyphenyl)-2-methylpropan-2-ylamino)-1-hydroxyethyl)-5-hydroxybenzo[d]thiazol-2(3H)-one acetate salt (R)-1-(5-tert-butoxy-2-isopropoxybenzo[d]thiazol-7-yl)-2-(1-(4-butoxyphenyl)-2-methylpropan-2-ylamino)ethanol, (1 equiv.) was suspended in isopropanol. At 50 to 60°, a 1M aqueous hydrochloric acid solution (3 equiv.) was added within about 30-60 min. After complete reaction (approx. 2.5 hours at 60° C.) the solution was cooled to 20° C. and sodium hydroxide 2M (3 equiv.) added gradually at this temperature. After complete addition the emulsified free base (R)-7-(2-(1-(4-butoxyphenyl)-2-methylpropan-2-ylamino)-1-hydroxyethyl)-5-hydroxybenzo[d]thiazol-2 (3H)-one was extracted into ethylacetate and the organic layer washed with water. The organic layer was treated with activated carbon and filtered using microcrystalline cellulose as a filter aid. The filter cake was washed with ethyl acetate. The filtrate, containing the free base (R)-7-(2-(1-(4-butoxyphenyl)-2-methylpropan-2-ylamino)-1-hydroxyethyl)-5-hydroxybenzo[d]thiazol-2(3H)-one, was carefully concentrated to a defined residual volume by distillation at a jacket temperature of 55° C. under reduced pressure. Isopropylacetate was then added and partly removed by distillation to a defined residual volume at a jacket temperature of 55° C. under reduced pressure. Further isopropylacetate and a solution of acetic acid in isopropylacetate were added to the warm distillation residue at 50-55° C. During the acetic acid addition the batch was seeded with (R)-7-(2-(1-(4-butoxyphenyl)-2-methylpropan-2-ylamino)-1-hydroxyethyl)-5-hydroxybenzo[d]thiazol-2(3H)-one acetate salt to initiate the controlled crystallization of the acetate salt early at 50-55° C. After gradually cooling to 0° C. the product suspension was filtered and washed twice with cold isopropylactetate. The filter cake was dried at 50 to 90° C. under reduced pressure until constant weight to give crystalline (R)-7-(2-(1-(4-butoxyphenyl)-2-methylpropan-2-ylamino)-1-hydroxyethyl)-5-hydroxybenzo[d]thiazol-2(3H)-one acetate salt at a typical yield of approx. 80%.

Example 4

(R)-7-(2-(1-(4-butoxyphenyl)-2-methylpropan-2-ylamino)-1-hydroxyethyl)-5-hydroxybenzo[d]thiazol-2(3H)-one glycolate salt 500 mg (1.161 mmol) of free base (R)-7-(2-(1-(4-butoxyphenyl)-2-methylpropan-2-ylamino)-1-hydroxyethyl)-5-hydroxybenzo[d]thiazol-2(3H)-one was suspended in 10.0 ml acetonitrile and 0.25 ml water in a 50 mL four-necked flask and paddle stirred at r.t. The suspension was heated at an internal temperature of 60° C. (jacket temperature 85° C.) and 90 mg 2-hydroxyacetic acid (1.161 mmol) added to the solution. 0.25 ml water was then added at an internal temperature of 60° C. The solution was seeded with (R)-7-(2-(1-(4-butoxyphenyl)-2-methylpropan-2-ylamino)-1-hydroxyethyl)-5-hydroxybenzo[d]thiazol-2(3H)-one glycolate at an internal temperature of 30° C. and stirred overnight (16 h) at r.t. Another 10 ml acetonitrile was added and stirred over the weekend at r.t. The suspension was filtered at r.t. through a glass filter and washed once with 1.0 ml acetonitrile/water 9:1 v/v and twice with 1.0 ml acetonitrile. 320 mg wet filter cake was dried in a drying oven overnight (16 h) at r.t. to dryness.

Preparation of (R)-7-(2-(1-(4-butoxyphenyl)-2-methylpropan-2-ylamino)-1-hydroxyethyl)-5-hydroxybenzo[d]thiazol-2(3H)-one glycolate seeds 63.0 mg (0.146 mmol) of free base (R)-7-(2-(1-(4-butoxyphenyl)-2-methylpropan-2-ylamino)-1-hydroxyethyl)-5-hydroxybenzo[d]thiazol-2(3H)-one and 11.24 mg (0.146 mmol) glycolic acid were dissolved in 1.0 ml acetonitrile and 0.05 ml water. The solution was stirred at r.t. with a magnetic stirrer. Precipitation took place overnight. The suspension was filtered at r.t. through a glass filter and washed three times with 0.5 ml acetonitrile. The wet filter cake was dried in a drying oven overnight (16 h) at r.t. to dryness. Yield: 52 mg white powder Examples 5, 6 and 7

XRPD and DSC analysis of crystalline (R)-7-(2-(1-(4-butoxyphenyl)-2-methylpropan-2-ylamino)-1-hydroxyethyl)-5-hydroxybenzo[d]thiazol-2(3H)-one and its acetate and glycolate salt forms XRPD analysis of free base crystalline (R)-7-(2-(1-(4-butoxyphenyl)-2-methylpropan-2-ylamino)-1-hydroxyethyl)-5-hydroxybenzo[d]thiazol-2(3H)-one and its acetate and glycolate salt forms was carried out under the following experimental conditions:

| XRPD method | |
|---|---|
| Instrument | Bruker D8 Advance (reflection) |
| Irradiation | CuKα (40 kV, 30 mA) |
| Step | 0.017 grd |
| Scan type | Continuous scan |
| Scan time | 107.1 s |
| Scan range | 2°-40° (2 theta value) |

DSC analysis was carried out under the following experimental conditions:

| DSC method | |
|---|---|
| Instrument | Perkin Elmer Diamond |
| Temperature range | 30°-300 C. |
| Sample mass | 2-3 mg |
| Sample pan | Aluminium closed |
| Nitrogen flow | 20-50 K/min |

Example 5

XRPD analysis of crystalline (R)-7-(2-(1-(4-butoxyphenyl)-2-methylpropan-2-ylamino)-1-hydroxyethyl)-5-hydroxybenzo[d]thiazol-2(3H)-one Free base (R)-7-(2-(1-(4-butoxyphenyl)-2-methylpropan-2-ylamino)-1-hydroxyethyl)-5-hydroxybenzo[d]thiazol-2(3H)-one was recrystallised as described below prior to XRPD analysis.

4.0 g (2.232 mmol) of (R)-7-(2-(1-(4-butoxyphenyl)-2-methylpropan-2-ylamino)-1-hydroxyethyl)-5-hydroxybenzo[d]thiazol-2(3H)-one was suspended in 24.0 ml ethyl acetate in a 100 ml four-necked flask and paddle stirred at r.t. The suspension was dissolved at an internal temperature of 70° C. (jacket temperature 90° C.) to provide a clear yellow solution. The solution was cooled down over 30 min. at r.t. and seeded with free base (R)-7-(2-(1-(4-butoxyphenyl)-2-methylpropan-2-ylamino)-1-hydroxyethyl)-5-hydroxybenzo[d]thiazol-2(3H)-one at an internal temperature of 35° C. (crystallisation taking place very slowly) and stirred overnight (16 h) at r.t. The solution was then filtered at r.t. through a glass filter (fast filtration, duration: <1 min.) and washed 3× with 2.0 ml ethyl acetate (clear yellow mother liquor). 5.82 g wet filter cake was dried in a drying oven overnight 16 h at r.t. and 16 h at 40° C. Yield: 3.63 g white powder (90.75%)

The crystalline (R)-7-(2-(1-(4-butoxyphenyl)-2-methylpropan-2-ylamino)-1-hydroxyethyl)-5-hydroxybenzo[d]thiazol-2(3H)-one was analysed by XRPD and the characteristic peaks are shown in the table below (see also FIG. 5). Of these, the peaks at 8.5, 13.3, 13.9, 14.4, 15.2, 17.2, 17.5, 18.1, 21.3 and 22.5° 2-theta are the most characteristic.

| Angle (2-Theta °) | Intensity % |
|---|---|
| 8.5 | medium |
| 11.4 | medium |
| 12.7 | medium |
| 13.3 | medium |
| 13.9 | medium |
| 14.4 | medium |
| 15.2 | medium |
| 17.2 | high |
| 17.5 | high |
| 18.1 | high |

-continued

| Angle (2-Theta °) | Intensity % |
|---|---|
| 21.3 | medium |
| 21.7 | high |
| 22.5 | high |
| 23.3 | high |
| 23.6 | medium |
| 24.4 | medium |
| 25.6 | medium |
| 26.1 | high |
| 26.6 | high |
| 27.9 | medium |
| 28.5 | medium |
| 28.9 | medium |

Crystalline free base (R)-7-(2-(1-(4-butoxyphenyl)-2-methylpropan-2-ylamino)-1-hydroxyethyl)-5-hydroxybenzo[d]thiazol-2(3H)-one was analysed by DSC and found to have an onset of melting at about 115° C.

Example 6

XRPD analysis of crystalline (R)-7-(2-(1-(4-butoxyphenyl)-2-methylpropan-2-ylamino)-1-hydroxyethyl)-5-hydroxybenzo[d]thiazol-2(3H)-one acetate salt Crystalline (R)-7-(2-(1-(4-butoxyphenyl)-2-methylpropan-2-ylamino)-1-hydroxyethyl)-5-hydroxybenzo[d]thiazol-2(3H)-one acetate salt was analysed by XRPD and the characteristic peaks are shown in the table below (see also FIG. 6). Of these, the peaks at 8.8, 11.5, 16.4, 17.6, 18.2, 19.6, 20.1, 20.8, and 21.1° 2-theta are the most characteristic.

| Angle (2-Theta °) | Intensity % |
|---|---|
| 8.8 | high |
| 10.0 | low |
| 11.5 | high |
| 14.2 | low |
| 14.6 | low |
| 15.7 | low |
| 16.4 | high |
| 17.6 | medium |
| 18.2 | high |
| 19.1 | low |
| 19.6 | medium |
| 20.1 | high |
| 20.8 | high |
| 21.1 | medium |
| 23.3 | medium |
| 26.2 | low |
| 26.6 | medium |
| 27.1 | medium |

Crystalline (R)-7-(2-(1-(4-butoxyphenyl)-2-methylpropan-2-ylamino)-1-hydroxyethyl)-5-hydroxybenzo[d]thiazol-2(3H)-one acetate salt was analysed by DSC and found to have a broad endotherm at around 170° C.

Example 7

XRPD analysis of crystalline (R)-7-(2-(1-(4-butoxyphenyl)-2-methylpropan-2-ylamino)-1-hydroxyethyl)-5-hydroxybenzo[d]thiazol-2(3H)-one glycolate salt Crystalline (R)-7-(2-(1-(4-butoxyphenyl)-2-methylpropan-2-ylamino)-1-hydroxyethyl)-5-hydroxybenzo[d]thiazol-2(3H)-one glycolate salt was analysed by XRPD and the characteristic peaks are shown in the table below (see also FIG. 7). Of these, the peaks at 8.7, 11.6, 16.1, 18.0, 19.8, 20.7, and 21.1° 2-theta are the most characteristic.

| Angle (2-Theta °) | Intensity % |
|---|---|
| 8.7 | high |
| 11.6 | medium |
| 16.1 | high |
| 17.4 | medium |
| 18.0 | high |
| 19.2 | medium |
| 19.8 | high |
| 20.7 | high |
| 21.1 | high |
| 22.6 | low |
| 23.1 | medium |
| 23.3 | medium |
| 23.7 | low |
| 26.2 | high |
| 26.8 | medium |
| 27.9 | low |
| 28.3 | low |

Crystalline (R)-7-(2-(1-(4-butoxyphenyl)-2-methylpropan-2-ylamino)-1-hydroxyethyl)-5-hydroxybenzo[d]thiazol-2(3H)-one glycolate salt was analysed by DSC and found to have an onset of melting at about 188° C.

Example 8

Method for the Preparation of a Pharmaceutical Formulation Suitable for Subcutaneous Administration of Compound A in Acetate Salt Form For 1.00 liter drug product solution approximately 900 g of water for injection is placed into a clean vessel suitable for pharmaceutical compounding. 50 g mannitol, 0.60 g acetic acid and 10 g benzyl alcohol is added and dissolved in the water for injection. 1.00 g of Compound A is then added and dissolved. pH is adjusted to the target value, for example 5.0, with 1N sodium hydroxide solution. Water for injection is then added to the target product solution weight of 1.016 kg. The drug product solution is sterile filtered through a 0.22 μm PVDF membrane into washed, depyrogenized vials, closed with sterile rubber stoppers and crimped. The vials are terminally sterilized by autoclaving.

Example 8a

Alternative Method for the Preparation of a Pharmaceutical Formulation Suitable for the Subcutaneous Administration of Compound A in Acetate Salt Form For 1.00 liter drug product solution approximately 900 g of water for injection is placed into a clean vessel suitable for pharmaceutical compounding. 50 g mannitol and 10 g benzyl alcohol is added and dissolved in the water for injection. 1.14 g of the acetate salt of Compound A is then added and dissolved. pH is adjusted to the target value, for example 5.0, with acetic acid solution. Water for injection is then added to the target product solution weight of 1.016 kg. The drug product solution is sterile filtered through a 0.22 μm PVDF membrane into washed, depyrogenized vials, closed with sterile rubber stoppers and crimped. The vials are terminally sterilized by autoclaving.

Example 9

Comparative Solubilities of Free Base, Acetate Salt and Glycolate Salt Forms of Compound A The relative solubilities of the free base form and the acetate and glycolate salt forms of Compound A were analysed and the results are show in the table below. Solutions were titrated with addition of HCl or NaOH for pH adjustment. The improved aqueous solubilities of the acetate and glycolate salt forms relative to the free base form of Compound A make the acetate and glycolate salts of Compound A more suitable for subcutaneous injection or infusion.

| Compound A free base solubility in $H_2O$ | | Compound A acetate salt solubility in $H_2O$ | | Compound A glycolate salt solubility in $H_2O$ | |
|---|---|---|---|---|---|
| pH | Conc in mg/mL | pH | Conc in mg/mL | pH | Conc in mg/mL |
| 6.2 | 0.27 | 5.9 | 1.33 | 5.1 | 13.1 |
| 7.0 | 0.05 | 6.0 | 1.11 | 5.3 | 6.39 |
| 7.3 | <0.01 | 6.1 | 1.10 | 5.4 | 4.47 |
| 7.8 | <0.01 | 6.2 | 0.55 | | |

Example 10

In Vitro Cellular Profiles of Compound of the Invention (Compound A), its Enantiomer (Compound B), its Racemate (Compound A/B) and Formoterol The compound of the invention (compound A) shows the following $EC_{50}$ values in Test 1 as described hereinbefore.

| | CHO cells[#] | | | Primary cells; cAMP response $EC_{50}$ ($E_{max}$ %) | | |
|---|---|---|---|---|---|---|
| | $EC_{50}$ ($E_{max}$ %) | | | Human | Rat | Rat |
| Compounds | β2 AR | β1 AR | α1A AR | skMC | skMC | cardiomyocytes |
| Formoterol | 0.7 nM (99%**) | 85 nM (86%**) | 190 nM | 0.2 nM | 0.9 nM | 2.9 nM |
| Compound A (R) | 5.6 nM (88%**) | 560 nM (32%**) | >10 μM | 0.7 nM (96%*) | 3.4 nM (98%*) | 5.7 nM (71%**) |
| Compound B (S) | 950 nM (83%**) | >10 μM | >30 μM | 280 nM (100%*) | n.d. | n.d. |
| Compound A/B | 11 nM (87%**) | 684 nM (38%**) | n.d. | 0.63 nM (100%*) | n.d. | n.d. |
| Compound A (R) acetate salt | 2.5 nM (91%) | n.d. | n.d. | 1.7 nM (93%) | n.d. | n.d. | skMC: differentiated skeletal myotubes;
*compared to formoterol;
**compared to isoprenaline;
[#]cAMP for β1 and β2, $Ca^{2+}$ for α1A;
n.d. not determined The compound of the invention (compound A) is a potent and selective β2 AR agonist with very low intrinsic efficacy on β1 AR and no activity on α1A AR. Its enantiomer Compound B is very weak on β2 AR with an $EC_{50}$ of 950 nM.

Example 11

Effects of Formoterol and Compound A on Skeletal Muscle and Heart Weight In Vivo Male Wistar Han IGS (International Genetic Standard) rats (Crl:WI(Han)) at the weight of 350-400 g were purchased from Charles River Laboratories. Rats were acclimated to the facility for 7 days. Animals were housed in groups of 3 animals at 25° C. with a 12:12 h light-dark cycle. They were fed a standard laboratory diet containing 18.2% protein and 3.0% fat with an energy content of 15.8 MJ/kg (NAFAG 3890, Kliba, Basel, Switzerland). Food and water were provided ad libitum. Formoterol or Compound A was dissolved in the vehicle indicated below to achieve a dose range of 0.003 to 0.03 mg/kg/day for formoterol and 0.01 to 0.1 mg/kg/day for Compound A with the Alzet model 2ML4 for 28 days. Pumps were filled with the solution and kept for several hours at 37° C. in PBS until surgical implantation. Rats were treated subcutaneously with Temgesic at a dose of 0.02 mg/kg with a volume of 1 ml/kg at least 30 minutes before surgery, and then the pumps filled with the solution indicated above were implanted subcutaneously into the back of the rats under anesthesia with isoflurane at a concentration of 3%. Temgesic was administered subcutaneously to the rats 24 h and 48 h after the surgery. Body weights were measured twice per week. Clips were removed 10 days after the surgery under anesthesia. Four weeks after the treatment, the rats were euthanized with $CO_2$, and the tibialis anterior, gastrocnemius and soleus muscles, heart and brain were dissected and weighed. Brain weight was used for normalization of organ weights. Results are expressed as mean+/−SEM. Statistical analysis was carried out using Dunnett's multiple comparison test following one-way analysis of variance to compare the treatment groups to the vehicle control group. Differences were considered to be significant when the probability value was <0.05: *: Statistical analyses were performed by GraphPad Prism version 5.0 (GraphPad Software, Inc., La Jolla, Calif.). Muscle weight was normalized to the body weight at day 0 (initial body weight) and heart weight was normalized by brain weight.

| Study 1: Formoterol | | | | |
|---|---|---|---|---|
| Group | Treatment | Dose (mg/kg) | Route | Regimen |
| 1 | Vehicle* | 0 | s.c. | Alzet minipump 2ML4 for 4 weeks |
| 2 | Formoterol | 0.003 | | |
| 3 | Formoterol | 0.01 | | |
| 4 | Formoterol | 0.03 | | |

*Vehicle: 20% 1:2 Cremophor:Ethanol in saline (0.9% NaCl)

| Study 2: Compound A | | | | |
|---|---|---|---|---|
| Group | Treatment | Dose (mg/kg) | Route | Regimen |
| 1 | Vehicle* | 0 | s.c. | Alzet minipump 2ML4 for 4 weeks |
| 2 | Compound A | 0.01 | | |
| 3 | Compound A | 0.03 | | |
| 4 | Compound A | 0.1 | | |

*Vehicle: 20% 1:2 Cremophor:Ethanol in saline (0.9% NaCl)

FIG. 1 shows that formoterol induces both skeletal muscle hypertrophy and heart mass increase to the same extent, while Compound A induces skeletal muscle hypertrophy with minimum impact on heart mass, indicating that Compound A exhibits a selective effect on skeletal muscle over cardiac muscle. Compound A significantly induces skeletal muscle hypertrophy by 11% at 0.01 mg/kg/day with steady state plasma concentration of ~0.2 nM, while there were no findings on the heart histopathology even at 0.1 mg/kg/day with steady state concentration of ~2 nM.

Example 12

Effects of Formoterol and Compound A on the Function of Isolated Organs (Left Atrium Contraction, Sino-Atrial Node Beating Rate and Automaticity of Whole Heart)

Method
Left Atrium Contraction:

The left atrium contraction assay was performed at Ricerca Biosciences, LLC (catalog no 407500 Adrenergic betel), using left atria from Dunkin Hartley Guinea pig with body weight of 600+/−80 g (Arch. Int. Pharmacodyn. 1971: 191:133-141.).

Sino-Atrial Node Beating Rate:

New Zealand white female rabbits were killed by exsanguination after a deep anesthesia using a mixture of ketamine/xylazine, i.v. The heart was quickly removed and placed in Tyrode's solution. This solution was continuously gassed with 95% $O_2$, 5% $CO_2$, and previously warmed to approximately 36±0.5° C. The right atrium was separated from the rest of the heart. The preparations were mounted in a tissue bath and kept at 37±0.5° C. for at least one hour stabilization. Action potentials (AP) were intracellularly recorded with a standard glass microelectrode filled with 3 M KCl, connected to a high input impedance-neutralizing amplifier (VF-180 microelectrode amplifier, Bio-Logic). The AP were displayed on a digital oscilloscope (HM-407 oscilloscope, HAMEG), analyzed by means of high resolution data acquisition system (Notocord software hem 4.2, Notocord SA, Croissy, France). After one hour of stabilization, compounds were added to the Tyrode's solution at the increasing concentrations, each concentration being maintained for 30 minutes. There was no wash-out between two concentrations. Electrophysiological measurements were made by analyzing action potentials during the experimental protocol at the end of the 30 minute perfusion period. The SA spontaneous frequency was evaluated by counting the number of beats every 10 seconds to express the results in number of beats per minute (bpm). Data were expressed as mean±SEM.

Automaticity: Automaticity was investigated in the isolated Langendorff perfused rabbit hearts, conducted by Hondeghem Pharmaceuticals Consulting N.V., B-8400 Oostende, Belgium. The tests were run in on hearts from albino female rabbits weighing about 2.5 kg and having an age of approximately 3 months. The compound effects were measured in a fully automated model using isolated rabbit heart perfused according to the Langendorff technique. The spontaneously beating heart is retrogradely perfused with increasing concentrations of the test item. One electrode is carefully placed on the left atrium in order to record the cycle length of the sinus node automaticity.

Figure 2A:
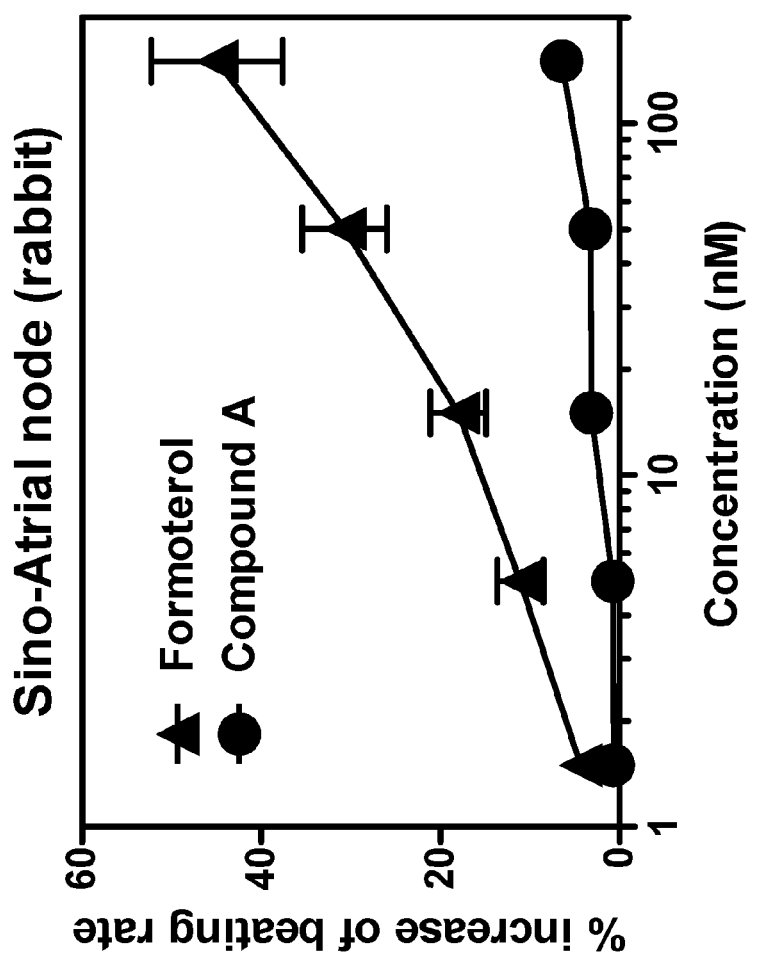
FIG. 2a shows the increase of beating rate in isolated rabbit sino-atrial nodes when using formoterol vs compound A (compound of the invention).
Figure 2B:
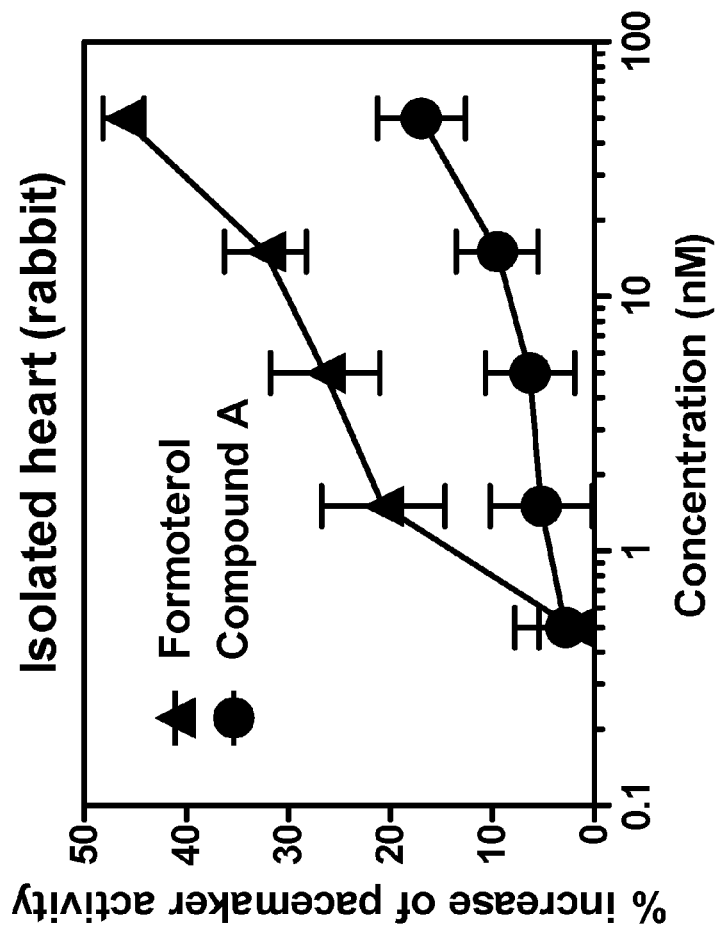
FIG. 2b shows the increase of pacemaker activity in isolated rabbit hearts when using formoterol vs compound A (compound of the invention).

FIGS. 2a and 2b show the results obtained when comparing formoterol with compound of the invention (compound A).

Compound A shows no effects on left atrium contraction up to 10 μM and less direct effects on the pacemaker activity, compared to Formoterol.

| | Formoterol | Compound A |
|---|---|---|
| Left atrium contraction $EC_{50}$ (n = 2) | 17 nM | >10 μM |
| Sino-Atrial node beating rate, maximum increase (n = 6) | +45% | +6.2% |
| Automaticity, maximum increase (n = 3) | +46% | +17% |

Values in FIGS. 2a and 2b are expressed as means ± SEM; Sino-atrial node (n = 6), isolated heart (n = 3)

Example 13

Effects of Formoterol and Compound A on the Heart Rate In Vivo

Wistar Han (W-H) IGS (International Genetic Standard) rats (Crl:WI(Han)) were purchased from Charles River Laboratories. Femoral arterial and venous catheters were chronically implanted and exteriorized through a spring tether-swivel system and housed in specialized cages. Arterial catheter was connected to a pressure transducer to continuously measure pulse pressure, mean arterial pressure and heart rate, which was derived from the blood pressure signal, via a digital data acquisition system. Compounds were administered via s.c catheter implanted through the skin buttun. Values are expressed as means±SEM (n=3).

Figure 3A:
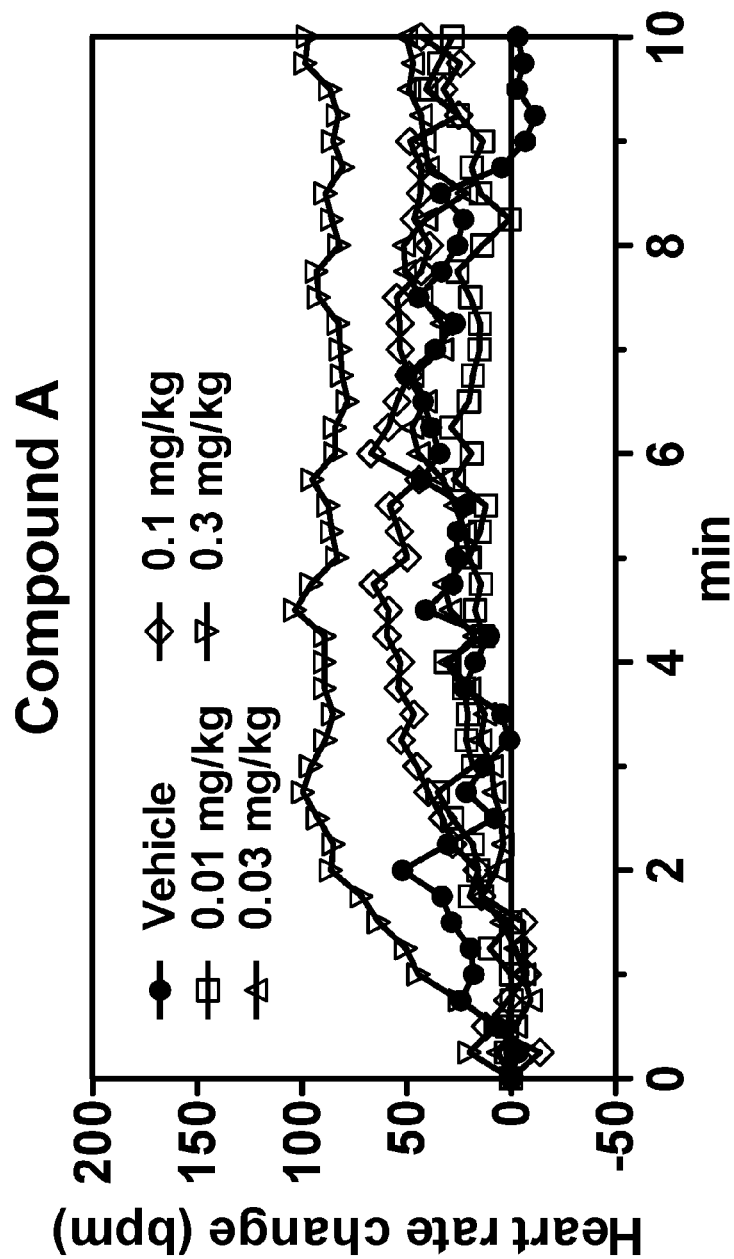
FIGS. 3a and 3b show the heart rate change in rats upon a s.c. bolus injection of Compound A (compound of the invention) or formoterol respectively.
Figure 3B:
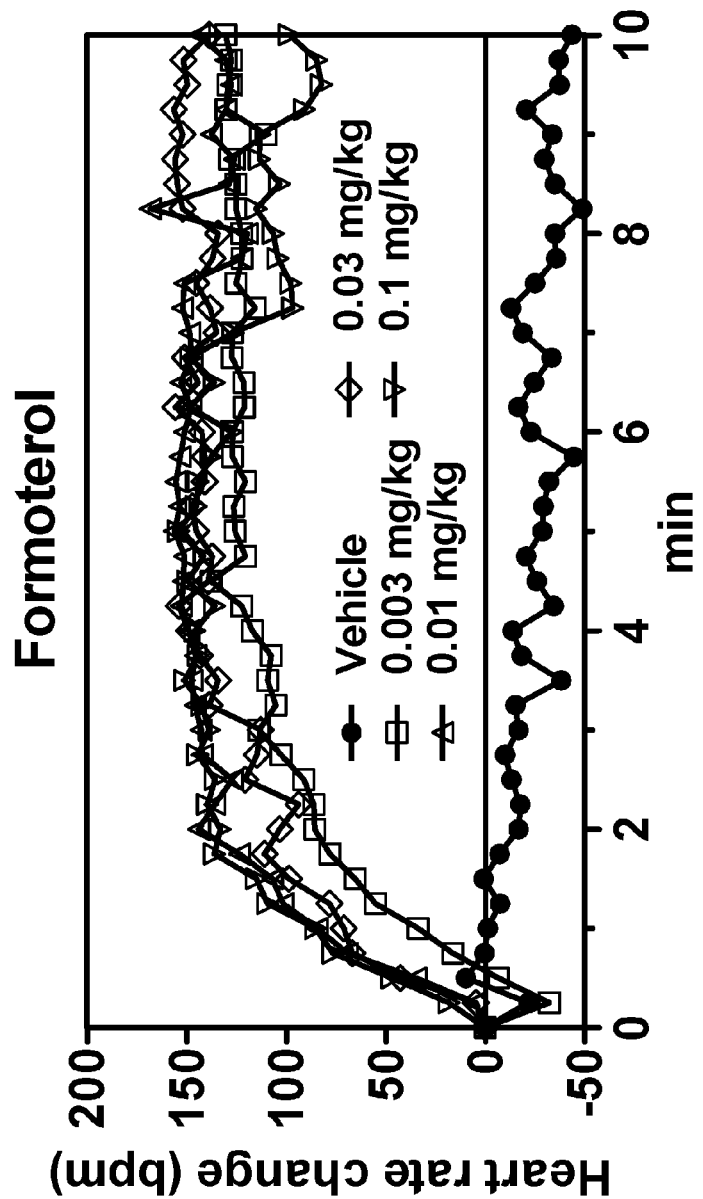
Figure 3C:
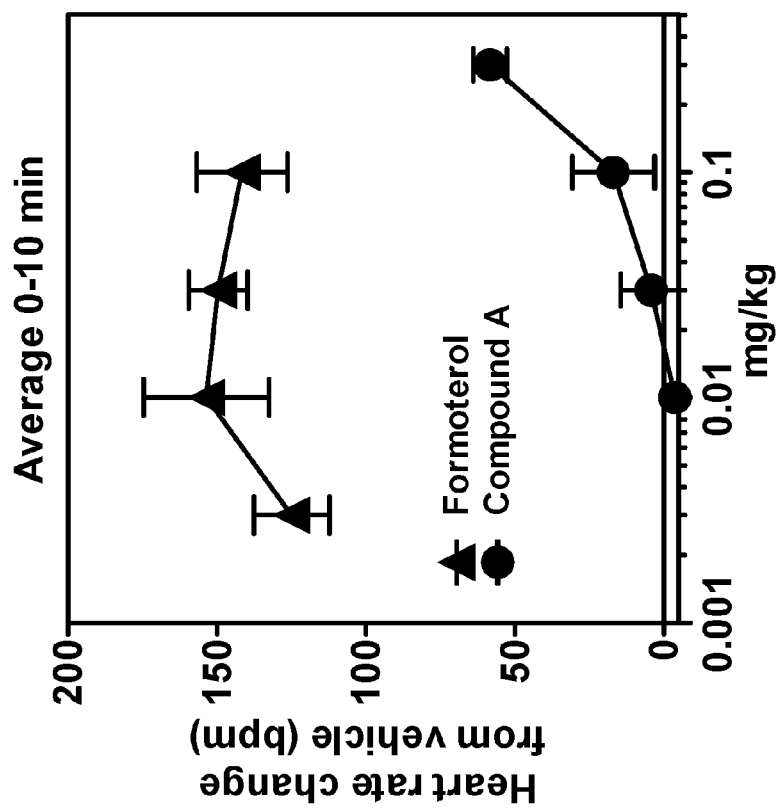
FIG. 3c compares the average heart rate change in rats when administering formoterol vs compound A (compound of the invention).

Compound A shows less heart rate increases compared to formoterol when administered with s.c. bolus, up to 0.3 mg/kg as shown in FIGS. 3a, 3b and 3c.

Example 14

Effects of Formoterol and Compound A on the Heart Rate In Vivo

Rhesus monkeys, 24 females with body weight around 4 to 8 kg, were randomized into 4 groups of n=6. The animals were restrained on a chair up to 4 hours after single subcutaneous administration of compounds, and then returned to their pens. Heart rates were measured using a Surgivet V3304 device. Values are expressed as means±SEM (n=6).

Figure 4A:
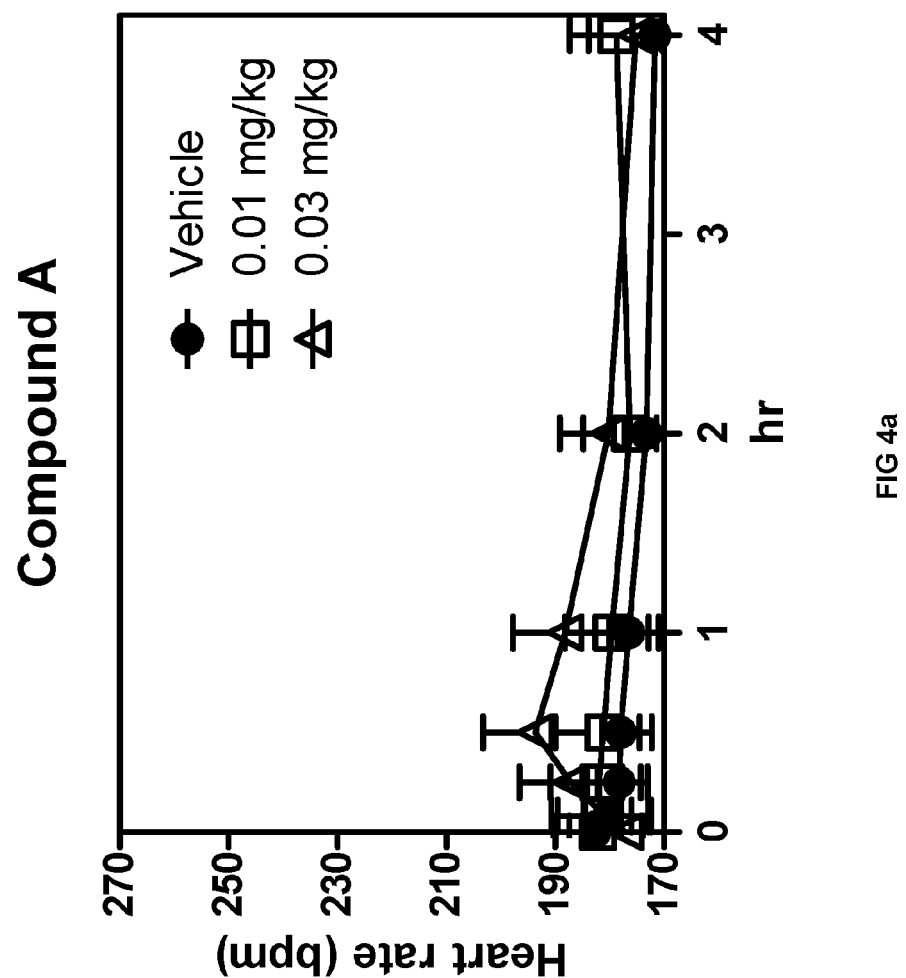
FIGS. 4a and 4b show the heart rate change in rhesus monkeys upon a s.c. bolus injection of Compound A (compound of the invention) or formoterol respectively.
Figure 4B:
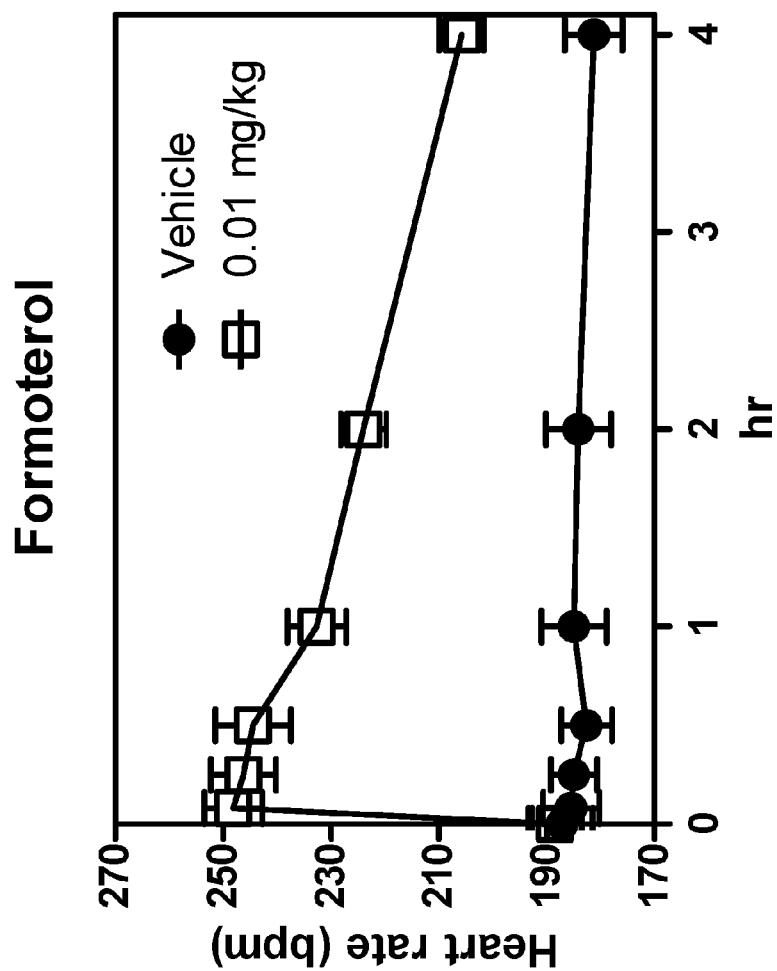

Compound A shows less heart rate increase compared to formoterol when administered as a s.c. bolus, up to 0.03 mg/kg as shown in FIGS. 4a and 4b.

Example 15

Effect of Compound A, its Enantiomer (Compound B) and its Racemate Compound A/B) on Serotonin 5-HT$_{2C}$ Receptor Human recombinant hr5-HT$_{2C}$ CHO cell membranes (Biosignal Packard, USA) and $^3$H-Mesulergine (NEN Life Science Products, USA, 1 nM) are used for measuring the binding affinity of the compounds to human 5-HT$_{2C}$ receptor. Non-specific binding is evaluated in the presence of 1 µM Mesulergine. Fifty µL each of membrane, ligand and compound in a total volume of 250 µL are incubated in 96-well plates for 60 min at 22° C. in a buffer containing 50 mM Tris, 0.1% ascorbic acid, 10 µM Pargyline, pH 7.7. The plates are filtrated, washed 3 times in ice-cold 50 mM Tris, dried and measured in Topcount.

CHO-K1 cells coexpressing mitochondrial apoaequorin, recombinant Serotonin 5-HT$_{2Cne}$ and the promiscuous G protein G$_{\alpha16}$, grown to mid-log phase in culture media without antibiotics were detached with PBS-EDTA, centrifuged and resuspended in assay buffer (DMEM/HAM's F12 with HEPES, without phenol red+0.1% BSA protease free) at a concentration of 1×10$^6$ cells/ml. Cells were incubated at room temperature for at least 4 h with coelenterazine h. Reference agonist was a-methyl-5-HT. For agonist testing, 50 µL of cell suspension were mixed with 50 µL of test or reference agonist in a 96-well plate. The resulting emission of light is recorded using Hamamatsu Functional Drug Screening System 6000 (FDSS 6000) luminometer. Agonist activity of test compound was expressed as a percentage of the activity of the reference agonist at its EC$_{100}$ concentration.

| Serotonin 5-HT$_{2C}$ | Binding | CHO EC$_{50}$ (E$_{max}$ %) |
| --- | --- | --- |
| 5-HT | n.d. | 0.24 nM |
| Compound A (R) | 11 µM | 280 nM (83%) |
| Compound B (S) | 0.8 µM | 19.7 nM (99%) |
| Compound A/B | 1.7 µM | 25 nM (113%) |

Compound A is 50-fold less active on 5-HT$_{2C}$ when compared to β2 AR agonist activity (5.6 nM), while its enantiomer Compound B is very weak on β2 AR with EC$_{50}$ of 950 nM but much more potent on 5-HT$_{2C}$ with EC$_{50}$ of 19.7 nM, showing inversed selectivity on the target.

Compound A is also over 10-fold less active on 5-HT$_{2C}$ when compared to the racemate or the (S) enantiomer, suggesting that the side-effect profile of this compound is advantageous.

The invention claimed is:

1. A method of treatment of a muscle wasting disorder comprising administering to a subject in need thereof a compound of formula (I) in free form or in pharmaceutically acceptable salt form which is

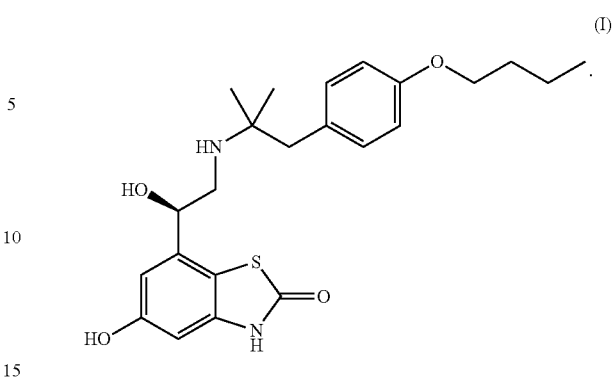

(I)

2. The method according to claim 1, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in free form.

3. The method according to claim 1, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in acetate salt form.

4. A method of inducing skeletal muscle hypertrophy comprising administering to a subject in need thereof a compound of formula (I) in free form or in pharmaceutically acceptable salt form which is

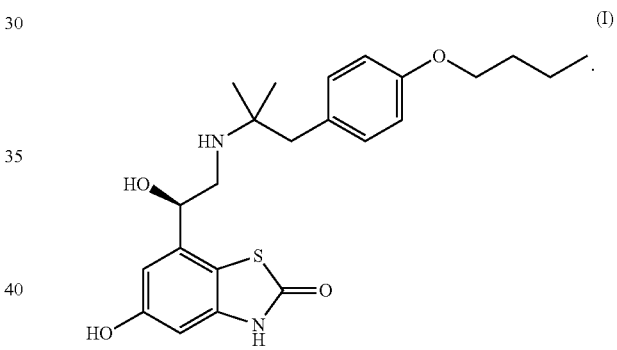

(I)

5. The method according to claim 4, wherein the hypertrophy is selective for skeletal muscle over cardiac muscle.

6. The method according to claim 4, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in free form.

7. The method according to claim 4, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in acetate salt form.

8. The method according to claim 5, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in free form.

9. The method according to claim 5, in which the compound of formula (I) is (R)-7-(2-(1-(4-butoxyphenyl)-2-methylpropan-2-ylamino)-1-hydroxyethyl)-5-hydroxy-benzo[d]thiazol-2(3H)-one in acetate salt form.

* * * * *